(12) United States Patent
Curro et al.

(10) Patent No.: US 6,808,791 B2
(45) Date of Patent: *Oct. 26, 2004

(54) APPLICATIONS FOR LAMINATE WEB

(75) Inventors: John Joseph Curro, Cincinnati, OH (US); Daniel Charles Peck, Cincinnati, OH (US); Saeed Fereshtehkhou, Cincinnati, OH (US); Anneke Margaret Kaminiski, Cincinnati, OH (US); Alfred Franc Baldwin, Jr., Greensboro, NC (US); Jessica Zingelmann Brown, Oak Ridge, NC (US); Edward Kenneth Stahl, Greensboro, NC (US); Charles Detwiler Roberson, Greensboro, NC (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/886,740

(22) Filed: Jun. 21, 2001

(65) Prior Publication Data

US 2002/0164465 A1 Nov. 7, 2002

Related U.S. Application Data

(63) Continuation-in-part of application No. PCT/US00/34746, filed on Dec. 20, 2000, and a continuation-in-part of application No. 09/584,676, filed on May 31, 2000, and a continuation-in-part of application No. 09/467,938, filed on Dec. 21, 1999.

(51) Int. Cl.[7] .............................. B32B 3/02; B32B 3/26; B32B 5/26; B32B 27/02
(52) U.S. Cl. .................. 428/198; 428/71; 428/72; 428/76; 428/158; 428/172; 428/196; 442/389; 442/392; 442/409; 239/53; 239/57
(58) Field of Search .................. 239/34, 53, 55–57; 428/68–76, 156, 172, 196, 198; 442/381, 389, 394, 409, 392

(56) References Cited

U.S. PATENT DOCUMENTS

| | | | |
|---|---|---|---|
| 2,257,428 A | 9/1941 | Ruegenberg |
| 2,679,887 A | 6/1954 | Doyle et al. |
| 2,862,251 A | 12/1958 | Kalwaites |
| 2,896,692 A | 7/1959 | Villoresi |
| 3,081,500 A | 3/1963 | Griswold et al. |
| 3,081,512 A | 3/1963 | Griswold |
| 3,354,021 A | 11/1967 | Dettre et al. |
| 3,485,706 A | 12/1969 | Evans |
| 3,542,634 A | 11/1970 | Such et al. |
| 3,574,109 A | 4/1971 | Yoshikawa |
| 3,597,299 A | 8/1971 | Thomas et al. |
| 3,681,182 A | 8/1972 | Kalwaites |
| 3,681,183 A | 8/1972 | Kalwaites |
| 3,695,967 A | 10/1972 | Ross |

(List continued on next page.)

FOREIGN PATENT DOCUMENTS

| | | | |
|---|---|---|---|
| EP | 0 112 654 A2 | | 7/1984 |
| EP | 0 207 904 | * | 1/1987 |
| EP | 0 127 483 B1 | | 10/1989 |
| EP | 0 164 740 B1 | | 4/1990 |
| EP | 0 432 755 B1 | | 5/1995 |

(List continued on next page.)

*Primary Examiner*—Cheryl A. Juska
*Assistant Examiner*—Jenna-Leigh Befumo
(74) *Attorney, Agent, or Firm*—Angela Marie Stone; Roddy M. Bullock

(57) ABSTRACT

A laminate web and several uses of the laminate web are disclosed. The laminate web comprises a first web, a second web joined to the first web at a plurality of discrete bond sites; and a third material disposed between at least a portion of the first and second webs. The laminate webs of the present invention are suitable for a variety of uses. Such uses include flexible carrying implement, medical applications, kitchen or bathroom implements, decorative coverings, home accent items, pet industry articles, fabric, fabric backings, edible materials, bedding applications, absorbent food pads, clean room wipes, tack cloths, and many other uses.

7 Claims, 12 Drawing Sheets

U.S. PATENT DOCUMENTS

| | | |
|---|---|---|
| 3,695,985 A | 10/1972 | Brock et al. |
| 3,728,203 A | 4/1973 | Taylor |
| 3,800,364 A | 4/1974 | Kalwaites |
| 3,855,046 A | 12/1974 | Hansen et al. |
| 3,860,003 A | 1/1975 | Buell |
| 3,881,987 A | 5/1975 | Benz |
| 3,927,673 A | 12/1975 | Taylor |
| 3,929,135 A | 12/1975 | Thompson |
| 3,949,127 A | 4/1976 | Ostermeier et al. |
| 3,953,638 A | 4/1976 | Kemp |
| 4,062,993 A | 12/1977 | Seward |
| 4,101,625 A | 7/1978 | Haley |
| 4,116,892 A | 9/1978 | Schwarz |
| 4,135,021 A | 1/1979 | Patchell et al. |
| 4,153,664 A | 5/1979 | Sabee |
| 4,207,367 A | 6/1980 | Baker, Jr. |
| 4,223,059 A | 9/1980 | Schwarz |
| 4,276,336 A | 6/1981 | Sabee |
| 4,285,100 A | 8/1981 | Schwarz |
| 4,333,979 A | 6/1982 | Sciaraffa et al. |
| 4,342,314 A | 8/1982 | Radel et al. |
| 4,349,020 A | 9/1982 | Krikorian |
| 4,355,066 A | 10/1982 | Newman |
| 4,404,052 A | 9/1983 | Persson et al. |
| 4,414,970 A | 11/1983 | Berry |
| 4,418,123 A | 11/1983 | Bunnelle et al. |
| 4,421,812 A | 12/1983 | Plant |
| 4,522,863 A | 6/1985 | Keck et al. |
| 4,525,407 A | 6/1985 | Ness |
| 4,573,991 A | 3/1986 | Pieniak et al. |
| 4,588,630 A | 5/1986 | Shimalla |
| 4,600,620 A | 7/1986 | Lloyd et al. |
| 4,603,069 A | 7/1986 | Haq et al. |
| 4,606,964 A | 8/1986 | Wideman |
| 4,609,518 A | 9/1986 | Curro et al. |
| 4,629,643 A | 12/1986 | Curro et al. |
| 4,657,802 A | 4/1987 | Morman |
| 4,695,278 A | 9/1987 | Lawson |
| 4,720,415 A | 1/1988 | Vander Wielen et al. |
| 4,741,944 A | 5/1988 | Jackson et al. |
| 4,758,297 A | 7/1988 | Calligarich |
| 4,797,310 A | 1/1989 | Barby et al. |
| 4,801,482 A | 1/1989 | Goggans et al. |
| 4,808,178 A | 2/1989 | Aziz et al. |
| 4,816,025 A | 3/1989 | Foreman |
| 4,840,829 A | 6/1989 | Suzuki et al. |
| 4,847,134 A | 7/1989 | Fahrenkrug et al. |
| 4,891,258 A | 1/1990 | Fahrenkrug |
| 5,116,662 A | 5/1992 | Morman |
| 5,143,679 A | 9/1992 | Weber et al. |
| 5,151,092 A | 9/1992 | Buell et al. |
| 5,156,793 A | 10/1992 | Buell et al. |
| 5,167,897 A | 12/1992 | Weber et al. |
| 5,204,158 A | 4/1993 | Phillips et al. |
| 5,260,345 A | 11/1993 | DesMarais et al. |
| 5,268,224 A | 12/1993 | DesMarais et al. |
| 5,320,891 A | 6/1994 | Levy et al. |
| 5,338,766 A | 8/1994 | Phan et al. |
| 5,376,198 A | 12/1994 | Fahrenkrug et al. |
| 5,431,991 A | 7/1995 | Quantrille et al. |
| 5,451,219 A | 9/1995 | Suzuki et al. |
| 5,518,801 A | 5/1996 | Chappell et al. |
| 5,536,555 A | 7/1996 | Zelazoski et al. |
| 5,567,501 A | 10/1996 | Srinivasan et al. |
| 5,587,225 A | 12/1996 | Griesbach et al. |
| 5,595,567 A | 1/1997 | King et al. |
| 5,620,779 A | 4/1997 | Levy et al. |
| 5,623,888 A | 4/1997 | Zafiroglu |
| 5,626,571 A | 5/1997 | Young et al. |
| 5,628,097 A | 5/1997 | Beńson et al. |
| 5,635,290 A | 6/1997 | Stopper et al. |
| 5,658,639 A | 8/1997 | Curro et al. |
| 5,662,634 A | 9/1997 | Yamamoto et al. |
| 5,681,302 A | 10/1997 | Melbye et al. |
| 5,683,374 A | 11/1997 | Yamamoto et al. |
| 5,683,794 A | 11/1997 | Wadsworth et al. |
| 5,691,035 A | 11/1997 | Chappell et al. |
| 5,714,107 A | 2/1998 | Levy et al. |
| 5,733,822 A | 3/1998 | Gessner et al. |
| 5,804,021 A | 9/1998 | Abuto et al. |
| 5,830,555 A | 11/1998 | Srinivasan et al. |
| 5,846,232 A | 12/1998 | Serbiak et al. |
| 5,851,935 A | 12/1998 | Srinivasan et al. |
| 5,853,881 A | 12/1998 | Estey et al. |
| 5,891,544 A | 4/1999 | Chappell et al. |
| 5,906,879 A | 5/1999 | Huntoon et al. |
| 5,916,661 A | 6/1999 | Benson et al. |
| 5,919,411 A | 7/1999 | Rezai et al. |
| 5,964,742 A * | 10/1999 | McCormack et al. ....... 604/380 |
| 6,015,605 A | 1/2000 | Tsujiyama et al. |
| 6,022,607 A | 2/2000 | James et al. |
| 6,025,050 A | 2/2000 | Srinivasan et al. |
| 6,027,593 A | 2/2000 | Lunt et al. |
| 6,054,202 A | 4/2000 | Takeuchi et al. |
| 6,057,024 A | 5/2000 | Mleziva et al. |
| 6,086,984 A | 7/2000 | DiMaggio, Jr. et al. |
| 6,106,925 A | 8/2000 | Palumbo |
| 6,203,654 B1 | 3/2001 | McFall et al. |

FOREIGN PATENT DOCUMENTS

| | | |
|---|---|---|
| EP | 0 432 763 B1 | 8/1995 |
| EP | 0 685 586 A2 | 12/1995 |
| EP | 0 687 757 A2 | 12/1995 |
| EP | 0 452 727 B1 | 3/1996 |
| EP | 0 758 543 A1 | 2/1997 |
| EP | 0 713 546 B1 | 3/1997 |
| EP | 0 677 284 B1 | 6/1999 |
| EP | 0 919 212 A2 | 6/1999 |
| EP | 0 945 251 A1 | 9/1999 |
| EP | 0 945 536 A2 | 9/1999 |
| EP | 0 955 159 A1 | 11/1999 |
| EP | 0 823 878 B1 | 8/2000 |
| JP | 08299385 A | 11/1996 |
| WO | WO 94/19179 A1 | 9/1994 |
| WO | WO 96/10979 A1 | 4/1996 |
| WO | WO 97/11662 A1 | 4/1997 |
| WO | WO 97/47264 A1 | 12/1997 |
| WO | WO 99/37476 A1 | 7/1999 |
| WO | WO 99/55273 A1 | 11/1999 |
| WO | WO 99/55532 A1 | 11/1999 |
| WO | WO 99/67081 | 12/1999 |
| WO | WO 00/76430 A1 | 12/2000 |
| WO | WO 01/45616 A1 | 6/2001 |

* cited by examiner

APPLICATIONS FOR LAMINATE WEB

CROSS REFERENCE TO RELATED APPLICATION

This application is: a continuation-in-part and claims priority of prior application PCT International Application Ser. No. US00/34746 (Case 7897R2) which designates the US, will publish in English, and was filed Dec. 20, 2000 in the names of Curro et al.; and a continuation-in-part and claims priority of prior application Ser. No. 09/584,676 (Case 7897R2), filed May 31, 2000 in the names of Curro et al.; and a continuation-in-part and claims priority of prior application Ser. No. 09/467,938 (Case 7897), filed Dec. 21, 1999 in the names of Curro et al.

FIELD OF THE INVENTION

This invention relates to several uses and applications of a multilayer laminate web. In some embodiments, the central layer or the entire multilayer laminate web is apertured.

BACKGROUND OF THE INVENTION

Laminate webs formed by the joining of discrete webs in a layered relationship are well known in the art. For example, often laminate nonwoven webs are utilized in disposable absorbent articles such as diapers and adult incontinence products. Such laminated webs can be used as a topsheet, backsheet, or side panels. One example of a laminate web is a film/nonwoven laminate useful for a stretch side panel of a disposable diaper. Nonwoven/nonwoven laminates are also utilized to provide additional bulk or softness to a web component. Likewise, film/film laminate webs can provide benefits by combining the characteristics of various films in a layered relationship. Laminate webs can also be called composite webs.

Less common examples of laminate webs include laminates of dissimilar materials. The materials may be dissimilar in mechanical tensile properties, thermal properties, or visual/tactile properties. For example, a nonwoven web may be joined to a relatively stiff fabric to provide for a soft surface feel to the fabric. The dissimilar materials may be joined by melt bonding, adhesive bonding, ultrasonic bonding, and the like. Bonding methods are often determined by the materials themselves, but often require adhesive bonding. For example, a laminate or composite of materials having widely differing melt properties may require an adhesive layer between laminate layers. Even materials having similar melt properties, such as nonwoven and thermoplastic film materials are often joined by adhesive for adequate bonding to prevent unwanted delamination. Although adhesive may be necessary, such processing methods can be expensive due to the addition of adhesive, and the resulting laminate is often relatively stiff, depending on the laminate materials and the level of adhesive added.

Often laminate webs are intended to combine properties of the constituent layers to achieve synergistic benefits. For example, EP-B-715,571 issued to Wadsworth discloses a multilayered nonwoven composite web intended for use as a substitute for a woven web such as a textile web. The web comprises at least a layer of thermoplastic man-made fibers and a layer of cellulose-based fibers. The cellulose-based fiber layer is disclosed as thermally bonded to the thermoplastic man-made fiber layers at spaced apart locations. However, it appears that thermal bonding between both, or all, the layers is necessary to produce the requisite bonding.

EP-A-112,654 issued to Haq, et al. discloses a laminate comprising two sheets of nonwoven fabric or the like having sandwiched between them a solid core material which may be a highly porous, optionally liquid-containing, polymer. The two outer sheets are bonded to each other, without involving the core material, by means of a plurality of small, spaced bonding points, for example, spot-welds. Preferably the core material is in continuous sheet form and is perforated to accommodate the bonding points. However, it appears it would present a significant processing problem to register the perforations of the core material in order to have the outer layers bonded therethrough.

For many purposes it is desirable to have an apertured nonwoven web, the apertured web being characterized by a plurality of openings, or perforations, in the web. Such apertures can provide for an open mesh appearance, as well as beneficial texture and cloth-like properties. Such apertured nonwoven webs can be made by methods known in the art. For example, EP-B-164,740 issued to Shimalla discloses an apertured non-woven fabric comprising a web of thermoplastic fibers is described. The fabric is formed with a multiplicity of fused patterned regions and adjacent substantially non-fused regions, there being apertures formed within a plurality of the fused patterned regions but not within the adjacent regions. The fabric is produced by heat embossing a non-woven web of thermoplastic fibers at a temperature above the softening point of the fibers whereby the regions of the web compressed by the projections of the embossing means become fused, and immediately thereafter drafting the embossed web so that apertures are formed in the fused patterned regions. However, it is not apparent that the method disclosed would produce a laminate of nonwoven webs, or a laminate of dissimilar materials.

Another beneficial method of aperturing a nonwoven web, including laminates of nonwoven webs is disclosed in EP-A-852,483, issued to Benson et al. Disclosed is a laminate material having, for example, at least one layer of a spunbonded web joined to at least one layer of a meltblown web, a bonded carded web, or other suitable material. Such apertured webs are useful as the topsheet in a disposable absorbent article. However, this disclosure does not teach laminating webs comprising dissimilar materials (e.g., materials of different material classes or having differing material properties).

A perforated multilayer elastic coversheet comprising an intermediate elastic layer between upper and lower nonwoven layers is disclosed in EP-A-784,461 issued to Palumbo. The upper and lower layers are connected to the intermediate layer only around the perimeters of the perforations. While providing an apertured, elastic laminate, it is not apparent that the method disclosed could produce laminates comprising thermally-dissimilar materials.

As mentioned, nonwoven webs are beneficial as components of disposable consumer products, such as diapers, incontinence briefs, training pants, feminine hygiene garments, and the like, as well as in wipes such as disposable wet wipes. However, used alone, such nonwovens are limited in the range of beneficial properties, including visual, tactile, strength or absorbent properties due to the limits of known methods of making, particularly as compared to woven or knitted materials. Importantly, laminates of nonwoven webs and other materials for use in disposable consumer products have heretofore been limited due to processing limitations, including incompatible materials (e.g., thermally dissimilar materials), cost considerations (e.g., adhesive lamination costs) or tactile properties (e.g., softness and visual aesthetics).

Nonwovens are also beneficial components of other consumer products, such as non-absorbent disposable garments, durable garments, automotive components, upholstered furniture, filtration media, and other consumer or commercial goods. Nonwovens used in these and other applications benefit from their wide range of visual and tactile properties. However, in many cases, the nonwovens used could benefit from being combined with other dissimilar materials in a composite web.

Accordingly, it would be desirable to have laminate webs of dissimilar material properties which are not dependent upon thermal compatibility of each constituent layer for structural integrity.

Additionally, it would desirable to have a laminate web comprising nonwoven webs and component webs of different material properties.

Additionally, it would be desirable to have a laminate web formed by joining the constituent layers without adhesive.

Further, it would be desirable to have an apertured laminate web having visually distinct regions giving a fabric-like or knit-like look and feel.

BRIEF SUMMARY OF THE INVENTION

A laminate web and several uses of the laminate web are disclosed. The laminate web comprises a first web, a second web joined to the first web at a plurality of discrete bond sites; and a third material disposed between at least a portion of the first and second webs. The bond site defines an elongated melt weakened region with an aspect ratio of at least about 2. The bond site has a longitudinal axis oriented in a first direction and a transverse axis oriented in a second direction orthogonal to the first direction. The third material may be apertured in regions adjacent the bond sites, such that the first and second nonwoven webs are joined through the apertures.

In one embodiment an apertured laminate web is disclosed, having a first extensible web having a first elongation to break, and a second extensible web joined to the first extensible web at a plurality of bond sites, the second extensible web having a second elongation to break. A third web material is disposed between the first and second nonwovens, the third web material having a third elongation to break which is less than both of the first or second elongations to break.

In a further embodiment, an apertured laminate web is disclose, having first and second extensible webs being joined at a plurality of discrete bond sites and a third material disposed between the first and second nonwoven webs. The first and second nonwoven webs are in fluid communication via the apertures and have distinct regions being differentiated by at least one property selected from the group consisting of basis weight, fiber orientation, thickness, and density.

The laminate webs of the present invention are suitable for a variety of uses. Such uses include flexible carrying implements, medical applications, kitchen or bathroom implements, decorative coverings, home accent items, pet industry articles, fabrics, fabric backings, edible materials, bedding applications, absorbent food pads, clean room wipes, tack cloths, and many other uses.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Figure 1:
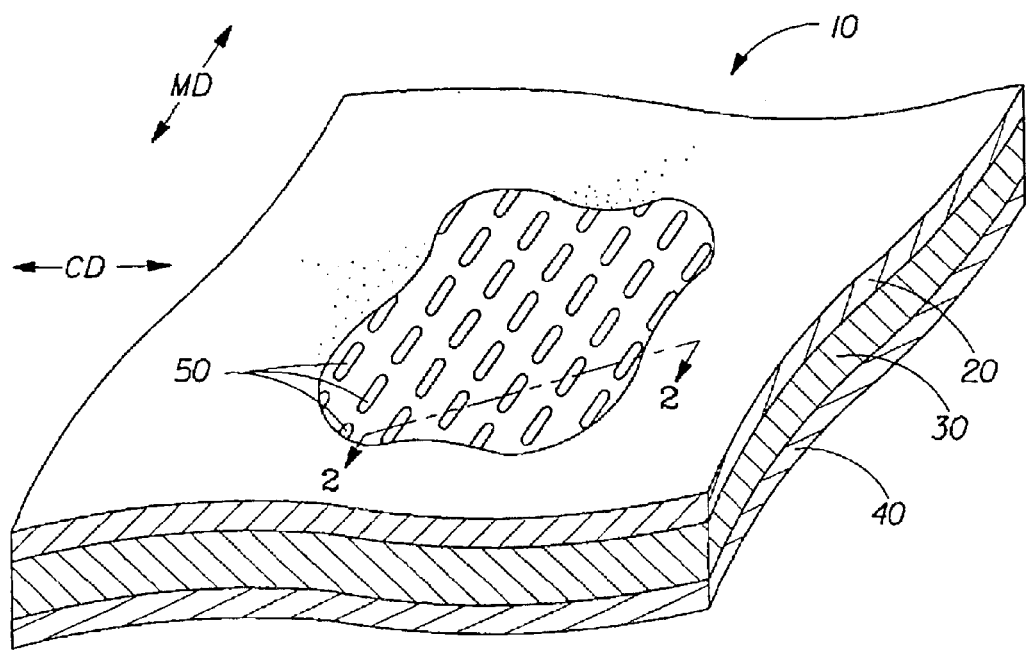
FIG. 1 is a perspective of one embodiment of a laminate web of the present invention.

As used herein, the term "absorbent article" refers to devices which absorb and contain body exudates, and, more specifically, refers to devices which are placed against or in proximity to the body of the wearer to absorb and contain the various exudates discharged from the body.

The term "disposable" is used herein to describe articles which are not intended to be laundered or otherwise restored or reused (i.e., they are intended to be discarded after a single use and, preferably, to be recycled, composted or otherwise disposed of in an environmentally compatible manner).

A "unitary" absorbent article refers to absorbent articles which are formed of separate parts united together to form a coordinated entity so that they do not require separate manipulative parts like a separate holder and liner.

As used herein, the term "nonwoven web" is used in its plain meaning as understood in the art and refers to a web that has a structure of individual fibers or threads which are interlaid, but not in any regular, repeating manner. Nonwoven webs have been, in the past, formed by a variety of processes, such as, for example, meltblowing processes, spunbonding processes and bonded carded web processes.

As used herein, the term "microfibers", refers to small diameter fibers having an average diameter not greater than about 100 microns.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "spunbonded fibers", refers to small diameter fibers which are formed by extruding a molten thermoplastic material as filaments from a plurality of fine, usually circular, capillaries of a spinneret with the diameter of the extruded filaments then being rapidly reduced by drawing.

As used herein, the term "unitary web" refers to a layered web comprising two or more webs of material, including nonwoven webs, that are sufficiently joined, such as by thermal bonding means, to be handled, processed, or otherwise utilized, as a single web.

As used herein, "laminate" and "composite" when used to describe webs of the present invention, are synonymous. Both refer to a web structure comprising at least two webs joined in a face-to-face relationship to form a multiple-layer unitary web.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiaotactic and random symmetries.

As used herein, the term "elastic" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches.

Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force. Such materials are denoted herein by the term "highly elastic" which refers to any material which upon application of a biasing force, is stretchable, that is, elongatable, at least about 200 percent (i.e., to a stretched, biased length, which is at least about 300 percent of its relaxed unbiased length), and which, will to within 105 percent of their initial relaxed length, upon release of the stretch force. Therefore, highly elastic materials are generally also elastic, but not all elastic materials are highly elastic.

As used herein, the term "nonelastic" refers to any material which does not fall within the definition of "elastic" above.

As used herein, the term "extensible" refers to any material which, upon application of a biasing force, is elongatable, at least about 25 percent without experiencing catastrophic failure. Catastrophic failure includes substantial tearing, fracturing, rupturing, or other failure in tension such that, if tested in a standard tensile tester, the failure would result in a sudden significant reduction in tensile force. As used herein, the term "highly extensible" refers to any material which, upon application of a biasing force, is elongatable, at least about 100 percent without experiencing catastrophic failure.

The Laminate Web

The laminate web 10 of the present invention comprises at least three layers or plies, disposed in a layered, face-to-face relationship, as shown in FIG. 1. The layers should be sufficiently thin to be processible as described herein, but no actual thickness (i.e., caliper) is considered limiting. A first outer layer 20, is preferably thermally bondable, and is preferably a nonwoven web comprising a sufficient quantity of thermoplastic material, the web having a predetermined extensibility and elongation to break. By "sufficient quantity" is meant a quantity of thermoplastic material adequate to enable enough thermal bonding upon application of heat and/or pressure to produce a unitary web. A second outer layer, 40, is preferably the same material as first outer layer 20, but may be a different material, also being thermally bondable and having a predetermined extensibility and elongation to break. At least one third central layer 30 is disposed between the two outer layers. The laminate web 10 is processed by joining means, such as by ultrasonic welding, or thermal calendaring as described below to provide a plurality of melt bond sites 50 that serve to couple the outer layers 20 and 40, and, in some embodiments, portions of central layer 30, thereby forming the constituent layers into a unitary web. When joined together, the two outer layers form an interior region between them. The interior region is the space between the outer layers surrounding the bond sites 50. In a preferred embodiment, the third central layer 30 substantially fills the interior region, the third central layer 30 being apertured coincident the bond sites 50.

While the laminate web 10 is disclosed primarily in the context of nonwoven webs and composites, in principle the laminate web 10 can be made out of any web materials that meet the requirements, (e.g., melt properties, extensibility) as disclosed herein. For example, the outer layers 20 and 40 can be thermoplastic films, micro-porous films, apertured films, woven fabrics, and the like. Central layer 30 can be paper, including tissue paper; metal, including metal foil; other non-thermoplastic web material, woven fabric, and the like. In general, it is required that outer layer materials be flexible enough to be processed as described herein. However, central layer can be a brittle, relatively stiff material, as long at it also can be processed as described herein, albeit possibly becoming fractured, broken, or otherwise broken up in the process. One of the unexpected advantages of the present invention, therefore, is the discovery that novel web properties can be exhibited by the choice of central layer 30 disposed between the two outer layers.

Non-Apertured Embodiment

Figure 2:
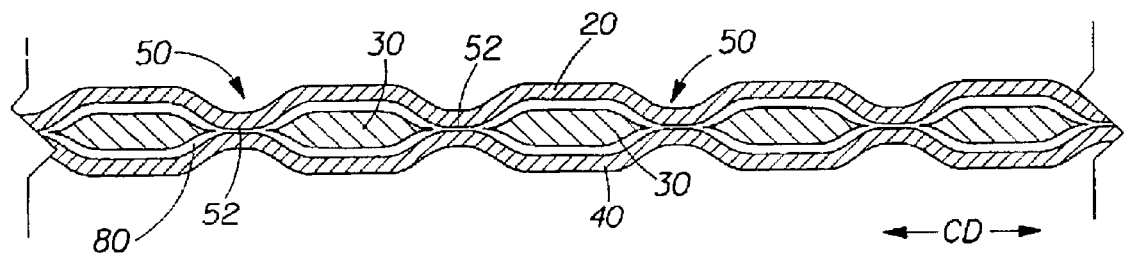
FIG. 2 is a cross-sectional view of a portion of the laminate web shown in FIG. 1.

In one embodiment, as shown in cross-section in FIG. 2, central layer 30 can be apertured, without aperturing the two outer layers to provide a three-layer laminate characterized by the laminate web 10 (as a whole) being un-apertured, while the central layer 30 is apertured. Importantly, the web of the present invention can be made by the method of the present invention without requiring registration of the layers to ensure bonding of the outer layers through the apertures of the central layer(s). One way of describing a preferred embodiment of a web 10 as described above, is that the unitary web 10, when viewed orthogonally by the un-aided human eye from a distance of approximately 50 cm, exhibits no apertures or perforations through the entire laminate, but bond sites 50 are nevertheless visible.

The laminate web 10 is further characterized in that the joining of the three plies into a unitary web can be achieved in the absence of adhesive. That is, in certain preferred embodiments no adhesive is required to bond the plies together; joining is achieved by the input of energy into the constituent layers, such as by thermal melt bonding of the two outer layers together at the melt bond sites 50. In other embodiments, the energy input can be via ultrasonic bonding. Accordingly, a significant benefit of the present invention is the provision of a laminate web, that is a unitary web, formed without the use of adhesives. Not only does this simplify processing and lower the cost of the laminate web, when certain materials such as nonwoven webs are used, it results in a more flexible, softer web.

As shown in FIG. 2, central layer 30 is chosen such that when the constituent web layers of laminate web 10 are processed by the method of the present invention, portions of central layer 30 in the region of the melt bond sites 50 separate to permit the first outer layer 20 to melt bond directly to the second outer layer 40 at the interface of the two materials 52 at melt bond sites 50. Thus, apertures in the central layer 30 are formed in the lamination step by displacement, just prior to the bonding of the outer layers as detailed by the method of the present invention below. In this manner, central layer 30 can be provided as an unapertured web, avoiding complex registration steps to align apertures in registry with bond sites when laminated. Further, central layer 30 need not be thermally compatible with outer layers 20 and 40. Central layer need not be a thermoplastic material, and need not even have a melting point. It simply needs to be displaceable by the forces exerted by the processing equipment as detailed below. Therefore, one way of describing the laminate web of the present invention is to distinguish the central layer as being a material differentiated from the materials of the first or second layers by at least one material property selected from thermal properties, elongation properties, elastic properties, or conductive properties. By "thermal properties" is meant primarily thermal melt properties, such that the central layer has no melting point, or if it has a melting point, it is preferably at least about 10 degrees Centigrade higher, more preferably about 20 degrees Centigrade higher than either outer layer, and can be 100 degrees Centigrade higher than either outer layer. By "elongation properties" is meant that in tension, the material of the central layer exhibits an elongation to break that is at least 10% less than either outer layer, more preferably 50% less than either outer layer, and can be greater than 100% less than either outer layer. Thus, the central layer can be extensible, while either outer layer can be highly extensible. By "elastic properties" is meant that the central layer can be, for example, elastic, while either outer layer can be highly elastic, as defined herein. Or the central layer can be non-elastic, and the outer layers elastic or highly elastic. By "conductive properties" as used herein is meant electrically conductivity, such that the central layer can have an electrical conductivity that is 10 times, and more preferably 100 or more times as great as the outer layers. Conductive properties may be facilitated by the central layer being a metallic foil, or by being a conductive polymer, including a conductive nonwoven web.

Another advantage of the method of the present invention is that, in some embodiments, e.g., for solid core central layer 30 materials (i.e., a continuous sheet, that is, not having substantial apertures, gaps, or other voids), it results in a unitary web having an apertured central layer 30 in full, intimate contact with the outer layers 20, and 40. By "full" and "intimate" is meant that central layer 30 fills all the unbonded regions between outer layers 20 and 40 such that outer layers 20 and 40 do not contact except at the bond sites 50. Of course, it is recognized that many materials of interest have significant air content, and filling "all" the unbonded region between outer layers 20 and 40 is not meant to imply that all air content is removed.

Figure 17A:
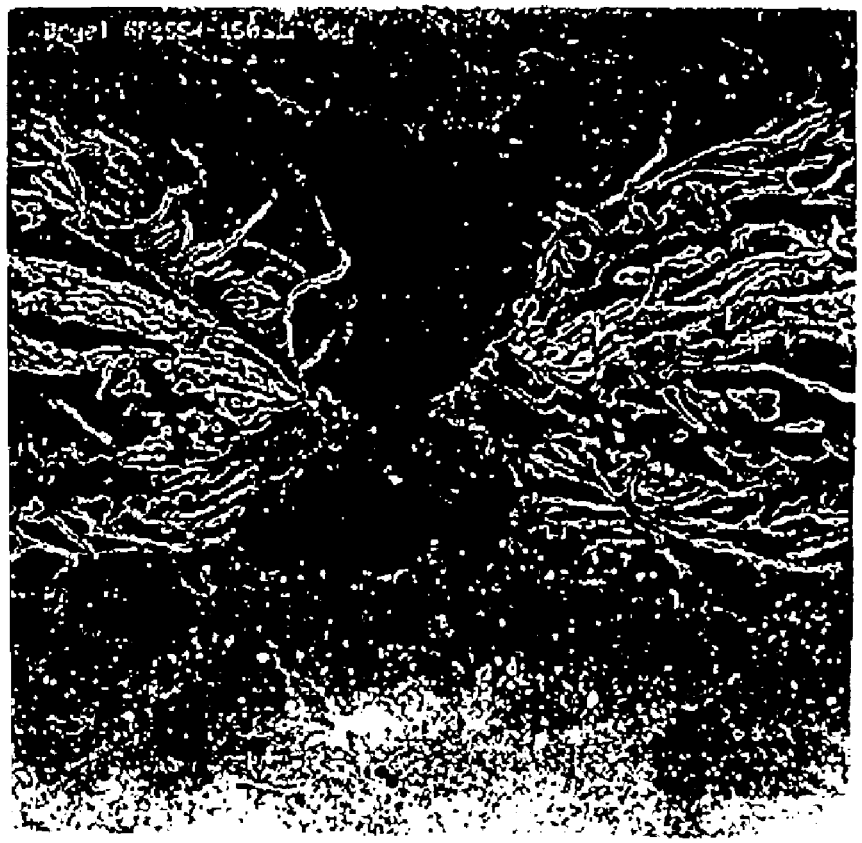
FIG. 17 A–B are cross-sectional photographs of a bond site before and after the tensioning step to form an aperture.
Figure 17B:

Central layer 30 can be involved, or participate, in the bonding between outer layers 20 and 40. By "involved" is meant that the central layer can, to some extent, be in intimate contact with, and possibly partially merged with, one or both immediate outer layers. The involvement may be due to actual melt bonding about the perimeter of bond site 50 (e.g., for thermoplastic central layers 30), or it may be due to mechanical interaction, such as by entanglement (e.g., for cellulosic fibrous central layer 30 between fibrous nonwoven layers), also about the perimeter of bond site 50. For example, FIG. 17-A shows in cross-section a unitary web comprising two outer nonwoven layers and a cellulosic tissue paper central layer. As can be seen, the lighter-colored central layer, due to the process of being "squeezed" apart, is intimately involved with the two outer layers at the bond site.

Without being bound by theory, it is believed that the process of the present invention facilitates such separation of central layer 30 by shearing, cutting, or otherwise fracturing the central layer 30, and displacing the material of the central layer 30 sufficiently to permit thermal bonding of the two outer layers 20 and 40. Thus, central layer 30 must be chosen to have properties that permit such displacement. Therefore, central layer 30 should have one or more of the properties of relatively low extensibility, relatively high frangibility, or relatively high deformability, such that the material of central layer 30 can be "squeezed" or otherwise displaced out of the region of thermal bond sites 50. Importantly, it is not required that the central layer 30 be melted out of the region of the thermal bond sites. Thus, central layer can be elastic, highly elastic, extensible, or highly extensible, depending on the desired end results and purposes of the resulting unitary web.

Figure 3:
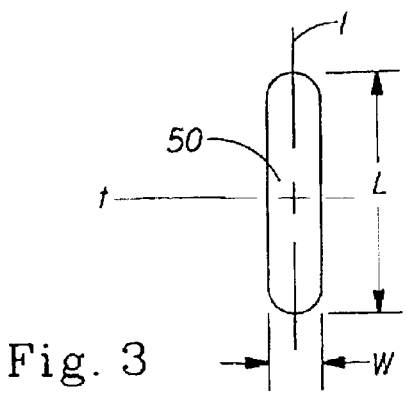
FIG. 3 is a magnified detail view of one bond site of a laminate web of the present invention.

Without being bound by theory, it is believed that to accomplish the displacement of central layer 30 to form apertures therein and to bond the outer layers, the thermal point calendaring described below should form thermal bond sites having a narrow width W dimension and a high aspect ratio. For example, FIG. 3 shows the melt area of a single melt bond site 50 having a narrow width dimension W and a high aspect ratio, i.e., the length, L, is much greater than the width, W. The length L should be selected to permit adequate bond area while width W is sufficiently narrow such that the protuberance used to form the bond site (as described below) can cut, shear, displace, or otherwise pierce the central layer 30 at the region of the bond sites by the method described below. Width W can be between about 0.003 inches and 0.020 inches, but in a preferred embodiment, is between about 0.005 inches and 0.010 inches, and may be adjusted depending on the properties of central layer 30.

It is believed that the aspect ratio of melt bond site 50 can be as low as about 2 (i.e., ratio of L/W equals 2/1). It can also be between about 2 and 100 or between about 3 and 50 or preferably between about 4 and 30. In one preferred embodiment, the aspect ratio was about 10 and in other embodiment about 25. It is believed that the aspect ratio of the melt bond sites 50 is limited only by the corresponding aspect ratio of the point bonding protuberances of the calendaring roller(s), as detailed below. The bond site may be described as an elongated melt weakened region with a longitudinal axis oriented in a first direction and a transverse axis oriented in a second direction orthogonal to the first direction.

In a preferred embodiment, the longitudinal axis of each bond site, 1, which corresponds directionally to the length dimension of bond site 50, is disposed in a regular, repeating pattern oriented generally parallel to the machine direction, MD as shown in FIG. 1. But the longitudinal axis of each bond site may be disposed in a regular, repeating pattern oriented in the cross machine direction, or randomly oriented in a mixture of cross and machine directions. For example, the bond sites 50 can be disposed in a "herringbone" pattern.

When nonwoven webs are used as constituent layers of laminate 10, an important distinction should be drawn between bond sites 50 which bond together outer layers 20 and 40 by the method of the present invention, and thermal bond sites that may be present in the constituent layers themselves. For example, nonwoven webs are typically consolidated by thermal bonding in a regular pattern of discrete spaced apart fused bonding areas, such as the pattern disclosed in U.S. Pat. No. 3,855,046 to Hansen et al., and the patterns shown generally in FIGS. 10 and 11 of U.S. Pat. No. 5,620,779 to Levy et al. Other films, nonwoven webs, and the like may have thermal embossments for aesthetic reasons. Therefore, in the unitary web 10 there may be many thermal bond sites, some of which are bond sites 50, and others which are bond sites in the base nonwoven, for example.

The bond sites of the base nonwoven do not typically have an aspect ratio greater than about 1, so that these bonds do not typically form apertures in the constituent layer during the stretching step disclosed below. Also, the spacing of such bond sites is typically a repeating pattern of bonded and unbonded area which may or may not provide for machine direction (MD) columns of bonded area next to columns of unbonded area. After forming bond sites 50, however, there is not likely to be any significant MD columns of unbonded areas; the overall bond pattern of any constituent nonwoven fabric is a combination of existing bonded areas and bond sites 50. Together the two sets of bond sites result in a complex pattern of bond sites that may or may not be described as columnar, regular, or uniform.

The resulting web of the present invention, as shown in cross-section in FIG. 2, is a laminate web 10 that is itself unapertured, but the central layer 30 is apertured coincident the regions of the bond sites 50. As stated above, by "unapertured" is meant that, on the whole, the laminate web 10 is considered unapertured. It is recognized that the un-apertured laminate web 10 of the present invention may have localized cut through, or tearing at bond sites 50 due to materials and processing variability or post lamination handling. Ideally, such cut through of the entire web is minimized and eliminated. Likewise, it is recognized that in some instances, there may not be complete displacement of the central layer 30 at all locations of bond sites 50 such that some localized portions of central layer 30 may not be apertured (and the outer layers not bonded). Nevertheless, the description herein is made for the laminate web 50 as a whole, and is not meant to be limited by aberrations or anomalies due to potential material or processing variables.

To produce the webs of the present invention, including as described in FIG. 2, the outer layers should have sufficient elongation to permit the necessary local deformation in the immediate vicinity of bond sites 50. Thus, the outer layers 20 and 40 can be extensible, highly extensible, elastic, or highly elastic.

The central layer 30 itself need not be thermally compatible with the outer layers. The central layer 30 need not even be melt processible. It can be, for example, a cellulosic material, such as paper; a metallic material, such as a metal foil; a woven or knit material, such as cotton or rayon blends; or a thermoset material, such as a polyester or aromatic polyamide film. The central layer 30 can be another nonwoven having suitable properties for processing into an apertured layer. If central layer 30 has a melting point, it is preferably at least about 10 degrees Centigrade higher, more preferably about 20 degrees Centigrade higher than the outer layers. In certain embodiments, for example a metal foil central layer 30 between thermoplastic nonwoven outer layers, the central layer can have a melting point at least 100 degrees Centigrade higher than the outer layers. However, central layer 30 need not have a melting point, and may simply experience softening at the calendaring temperatures required to bond the laminate. In certain central layer materials, such as metal foils, there may not be any softening due to thermal processing of the web.

The wide range of possible central layer materials permits a surprising variety of structures of the present invention, each having beneficial application in a wide assortment of end uses. For example, when outer layers of nonwoven material are used with a central layer of metal foil, the resulting laminate is a flexible, soft, formable, conductive web that is relatively quiet when folded, crumpled or otherwise deformed. Such a material can be used in applications requiring electrical shielding, for example. When a central layer of tissue paper is used, the resulting laminate is a soft, bulky, absorbent web. Such a laminate is suitable for use as a wiping implement, for example. Further, since the laminate web 10 is formed without the use of thermoplastic adhesives, durable, garment-like properties can be obtained. Such laminates can be laundered a number of times before suffering unacceptable wear.

By way of example, laminate web 10 can be a conductive fabric comprising relatively non-conductive thermoplastic outer layers 20 and 40 and a relatively conductive central layer 30. The outer layers can be non-woven webs for a low cost, soft, breathable conductive fabric. The central layer can be a metal foil, such as a copper foil or an aluminum foil. The central layer can also be a conductive polymer, a non-foil conductive fabric, or a composite conductive material. In general, as a conductive fabric embodiment, the outer layers should serve to insulate the conductive central layer (s). In a preferred three-layer embodiment the outer layers each have a first electrical resistance and the central layer has a second electrical resistance which is at least one-tenth the first electrical resistance, more preferably one-hundredth (i.e., the central layer is 10 times, preferably 100 times as conductive as the outer layers).

A conductive laminate web 10 can find use as a sheet of conductive material for signal propagation. It can also find use as a shielding material. In particular, the aspect ratio of the bond sites 50 can be predetermined for particular shielding characteristics. By altering the length, width, and orientation of the bond sites 50 certain wave propagation of electromagnetic waves can be altered or stopped. For example, the bond sites 50, which represent penetration of the conductive central layer, can be designed to be effective in filtering certain wavelengths of electromagnetic radiation. In addition to the electrical characteristics of such a web, the laminate web 10 can be, and preferably is, very flexible and formable, such that the conductive or shielding benefits can be applied in a non-planar fashion. For example, sensitive electronic equipment can be wrapped with a fabric shield.

A further benefit of the present invention is the capability to combine both thermoplastic and non-thermoplastic materials without any adhesives, to provide fabric-like composites having unique physical properties. For example, a material having high tensile strength and resistance to tear can include as a central layer 30 TYVEK®, available from DuPont, Wilmington Del., USA. TYVEK®, and equivalent or similar materials under other tradenames, is an extremely strong but breathable polyolefin nonwoven, commonly used as a house-wrap layer. However, it is not soft and clothlike, but has the look and feel of a plastic film. When used in a laminate web 10 of the present invention, for example with nonwoven outer layers, the laminate web exhibits the softness of a nonwoven with the strength of the TYVEK® layer. Again, this laminate can be, and is preferably, made without the use of adhesives to bind the web into a unitary web.

Further, relatively strong materials such as TYVEK® can be combined with additional central layers 30 to make laminate webs 10 having a variety of physical properties. For example, a laminate web comprising a TYVEK® layer can also comprise an absorbent layer, such a layer of absorbent tissue paper, such as BOUNTY® paper towel, available from The Procter & Gamble Co., Cincinnati Ohio, USA and one or more outer layers of polyethylene nonwoven (e.g. Corolind, available from BBA, Simpsonville, S.C., USA). Such a composite formed according to the method of the present invention can be transformed into a highly textile-like material, exhibiting the unusual combined properties of relatively high absorbency (from the BOUNTY® paper towel layer(s)), and relatively high strength (from the TYVEK® layer(s)).

Apertured Embodiments

A further benefit of the present invention is obtained when the non-apertured thermally bonded laminate web described above is stretched or extended in a direction generally orthogonal to the longitudinal axis, 1, of melt bond sites 50. The melt bonding at the melt bond sites 50 tends to make localized weakened portions of the web at the bond sites. Thus, as portions of the web 10 are extended in a direction generally orthogonal to the longitudinal axis 1 of bond sites 50, the material at the bond site fails in tension and an aperture is formed. The relatively high aspect ratio of melt bond sites 50, permits a relatively large aperture to be formed upon sufficient extension. When the laminate web 10 is uniformly tensioned, the result is a regular pattern of a plurality of apertures 60 corresponding to the pattern of melt bond sites 50.

Figure 4:
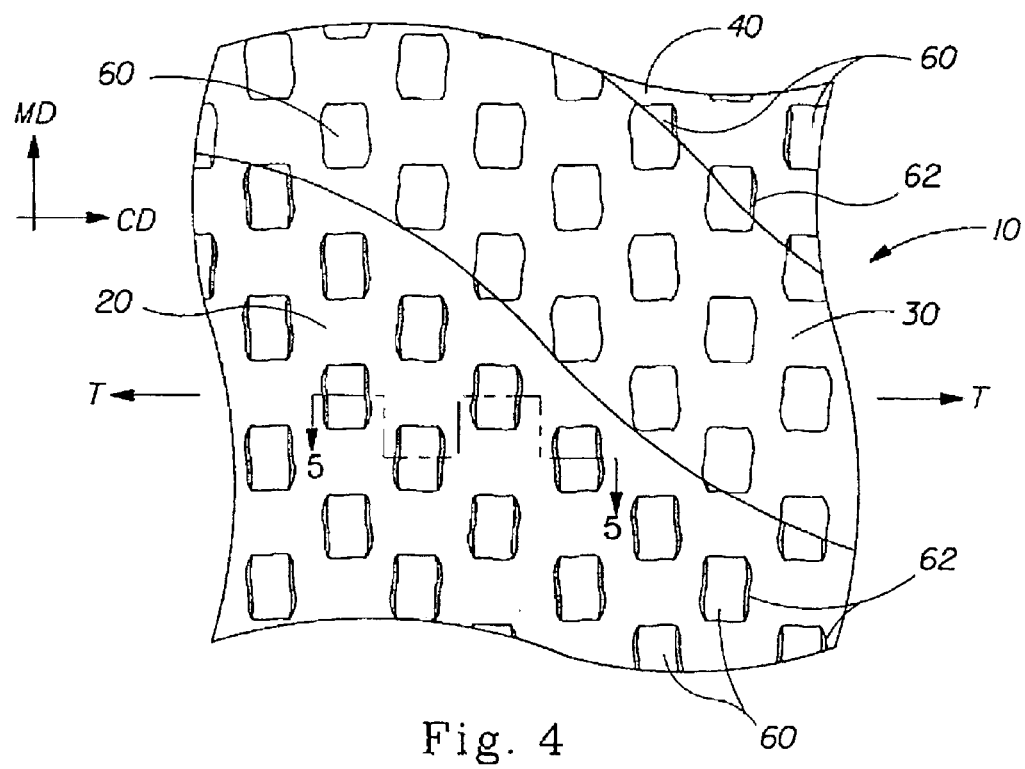
FIG. 4 is a top plan view of another embodiment of the laminate web of the present invention.

FIG. 4 shows a partially cut-away representation of an apertured laminate of the present invention. As shown, the partial cut-away permits each layer or ply to be viewed in a plan view. The laminate web 10 shown in FIG. 4 is produced after the thermally bonded laminate is stretched in a direction orthogonal to the longitudinal axis of the melt bond sites, in this case, in the cross-machine direction, CD with sufficient elongation in the direction of extension to cause apertures to form. As shown, where formerly were melt bond sites 50, apertures 60 are produced as the relatively weak bond sites fail in tension. Also as shown, central layer 30 can remain generally uniformly distributed within laminate 10, depending on the material properties of central layer 30. For example, if central layer 30 is more extensible than outer layers 20 or 40, then it simply extends, either elastically or by plastic deformation, but remains generally uniformly distributed in the unapertured regions of web 10. For example, if a thermoplastic film is utilized as the central layer 30, it extends, either extensibly or elastically (depending on the type of film), but can remain generally uniform, for example, in density or basis weight.

When apertures 60 are formed, the thermally bonded portions of outer layers 20 and 40 remain primarily on the portions of the aperture perimeters corresponding to the length dimension of bond sites 50. Therefore, each aperture 60 does not have a perimeter of thermally bonded material, but only portions remain bonded, represented as 62 in FIG. 4. One beneficial property of such a laminate web is that once apertured, fluid communication with the central layer is facilitated. Thus, an absorbent central layer 30 can be used between two relatively non-absorbent outer layers, and the laminate 10 could be an absorptive wiper with a relatively dry to the touch outer surface.

Figure 5:
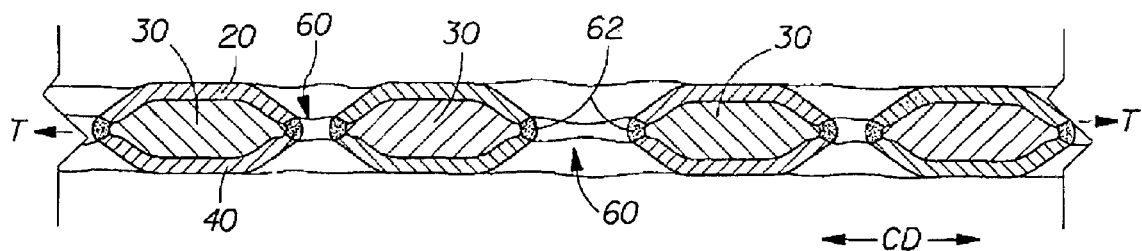
FIG. 5 is a cross-sectional view of a portion of the laminate web shown in FIG. 4.

To the extent that central layer 30 is involved, or participates, in any bonding between outer layers 20 and 40, it also participates in the remnant of bonded portions 62, as shown in FIG. 4. The involvement may be due to some degree of actual melt bonding about the perimeter of bond site 50 (e.g., for thermoplastic central layers 30), or it may be due to mechanical interaction, such as by entanglement (e.g., for cellulosic fibrous central layer 30 between fibrous nonwoven layers). FIG. 5 is a schematic representation of the cross-section denoted in FIG. 4. As shown, apertures 60 form when the laminate web is elongated in the direction T.

Another benefit of the present invention is obtained when the laminate is extended as described with reference to FIG. 4, but the central layer 30 is chosen to have an elongation to break less than either of the two outer layers, and less than the actual magnitude of extension. Thus, upon extension of the laminate web generally orthogonal to the longitudinal axis, 1, sufficient to form apertures in outer layers 20 and 40 (and thus the entire laminate web 10) central layer 30 fails in tension. Therefore, central layer 30 fractures (i.e., fails in tension) upon sufficient extension, such that after extension central layer 30 is no longer uniformly distributed over the non-apertured regions of the laminate web 10.

An example of one embodiment of a unitary web having a central layer having an elongation to break less than either of the two outer layers, and less than the actual magnitude of extension, is shown partially cut-away in FIG. 5. The partial cut-away permits each layer or ply to be viewed in a plan view. As shown, after extension, central layer 30 becomes fragmented, forming discontinuous regions of the central layer material. These discontinuous regions may be relatively uniformly distributed, such as in rows as shown in FIG. 5, or may be relatively randomly distributed, depending on the pattern of melt bond sites 50, the physical properties of central layer 30, and the method of extension employed.

One example of a web 10 having a structure similar to that shown in FIG. 5 is a web having outer layers of relatively extensible nonwovens, with a central layer of relatively low extensibility tissue paper. Such a laminate would be an apertured laminate web having an absorbent central core, wherein the absorbent core material is in fluid communication with regions exterior to the laminate web. That is, for example, if such a laminate web comprised nonwoven outer layers, it could be used as an absorbent wiper. Fluids could thus be absorbed via the apertures, the perimeter of which can be open at portions which provide fluid communication to the absorbent central core. If a relatively hydrophobic nonwoven web is used for the outer layers, such a wiper could exhibit dry-to-the-touch properties along with high absorbency.

One example of a web 10 having a structure similar to that shown in FIG. 5 is a web having outer layers of relatively extensible nonwovens, with a central layer of relatively low extensibility tissue paper. One particularly interesting structure incorporates a highly hydrophobic outer layer combined with a highly absorbent central layer. A suitable hydrophobic material is described in U.S. Pat. No. 3,354,022 Dettre et al. Such a material has a water repellent surface having an intrinsic advancing water contact angle of more than 90 degrees and an intrinsic receding water contact angle of at least 75 degrees. Such a material exhibits extremely hydrophobic properties, similar to the effect known to exist on leaves from the Lotus plant. When such a material is combined with an absorbent central layer, such as a BOUNTY® paper towel tissue layer, the resulting composite can be highly absorbent while retaining a very clean and dry outer surface. The basis weight and porosity of the outer layer can be varied to achieve different degrees of absorbent performance. In one embodiment the laminate could also be post-laminated to a fluid-impervious backing layer to form an absorbent fluid barrier. The fluid-impervious backing layer could be a flexible polymeric film for use such absorbent articles as sanitary napkins, diapers, place mats, floor mats, protective covers, and the like.

Figure 6:
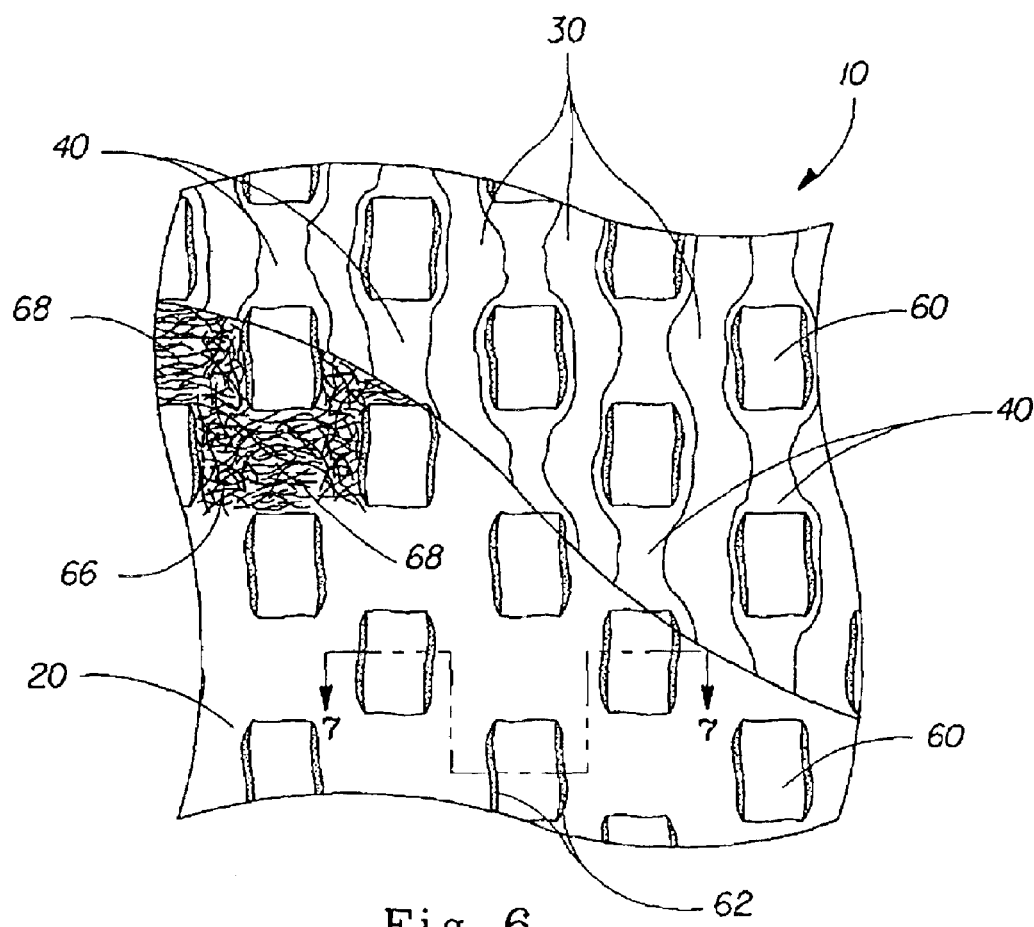
FIG. 6 is a top plan view of another embodiment of the laminate web of the present invention.

One surprising beneficial characteristic of the laminate web structure of the present invention described with reference to FIG. 6 is the presence of distinct regions in the non-apertured portion of the web being differentiated by at least one property selected from the group consisting of basis weight, thickness, or density. As shown in the cross-section of FIG. 7, several such regions can be differentiated. In a preferred embodiment, the regions are visually distinct, giving the laminate an aesthetically pleasing look and feel. The regions may also give the laminate a garment-like or knit-like texture and hand.

Figure 7:
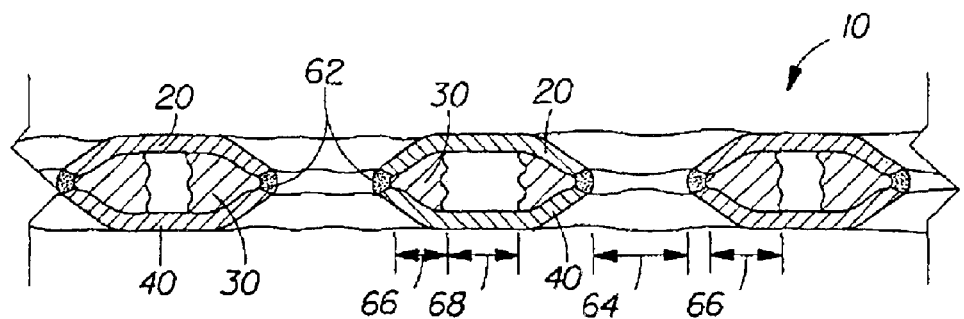
FIG. 7 is a cross-sectional view of a portion of the laminate web shown in FIG. 6.

With reference to FIG. 7, several structurally distinct regions can be identified in the cross-section shown. The region denoted 64 corresponds to the aperture 60. In the non-apertured area of the web, a region 66 is a relatively high basis weight region comprising central layer 30. Region 68 represents the portion of the laminate web in which central layer 30 has fractured and separated, i.e., is no longer fully present, forming a relatively low basis weight region of web 10. In general, the higher basis weight regions will also be correspondingly higher density regions, but need not be so. For example, a post-extension embossing process can be applied to web 10 to form regions of multiple densities in addition to the regions of multiple basis weight. For either the high basis weight regions or the high density regions, often the differences can be discernible by simply rubbing the laminate web between the fingers.

In general, for a laminate web 10 having generally parallel rows of melt bond sites 50 extending in the machine direction MD, which correspondingly form generally parallel rows of apertures when extended, and having a central layer with a lower elongation to break than the outer layers, the resulting extended, apertured laminate web 10 is characterized by generally low basis weight, low density regions between the apertures in the machine direction, MD, e.g., region 68 in FIGS. 6 and 7. Likewise, such a laminate web 10 is characterized by relatively high basis weight, high density regions between adjacent rows of apertures in the cross-machine direction, CD, e.g., region 66 in FIG. 7. By choice of central layer material 30 and possibly post laminating operations, e.g., an embossing process, the thickness of the laminate web can likewise be varied, the thicker regions generally corresponding to the higher density regions.

On particularly useful embodiment of a laminate web as described with reference to FIG. 7, is a conductive fabric for signal transmission via a plurality of closely-spaced, parallel signal conductors. For example, if a conductive metal foil is used as central layer 30, upon sufficient extension in the CD by the incremental stretching operation described below, the metal foil fractures into a plurality of discrete conductive ribbons corresponding to the high basis weight region 66 of FIG. 7. Outer layers 20 and 40 are preferably chosen for their insulating properties, and are, therefore, preferably thermoplastic polymeric material. For high-speed transmission of electrical signals, a low-dielectric material, such as polytetrafluoroethylene (PTFE), and preferably expanded PTFE (e.g., GORE-TEX® available from W. L. Gore and Associates, Newark, Del., USA) can be used as the insulating outer layers. Additional outer layers can be added (e.g., post laminate formation), including additional conductive layers to form a shielded ribbon cable. Another embodiment of a laminate web of the present invention utilizing nonwoven webs as the outer layers is characterized by distinct regions differentiated by fiber orientation. Differential fiber orientation can be achieved by providing for localized regions within the web that experience greater extension than other regions. For example, by locally straining the web 10 to a greater degree in the regions corresponding to regions 68 in FIG. 6, regions of significant fiber reorientation are formed. Such localized straining is possible by the method of the present invention detailed below.

Figure 8:
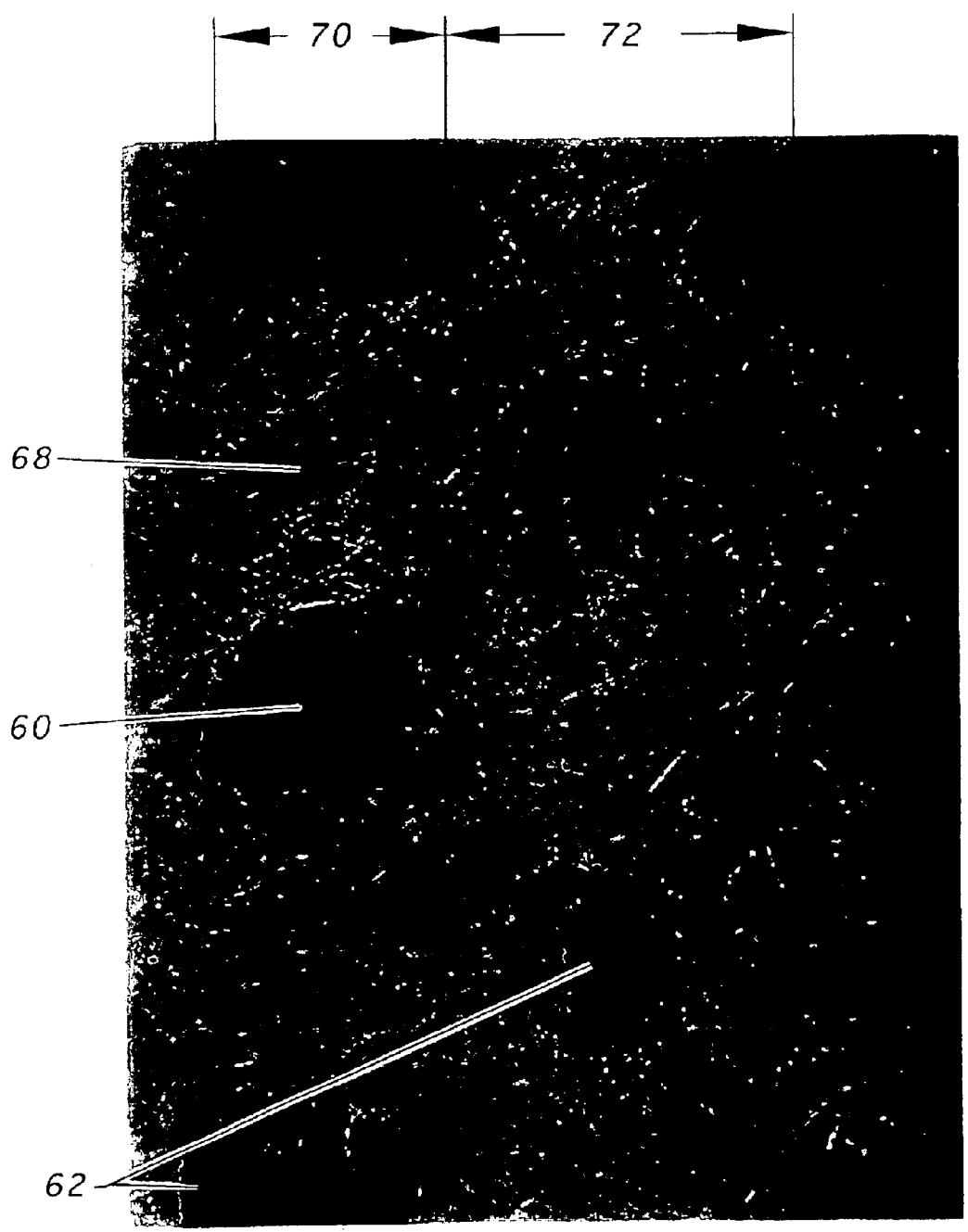
FIG. 8 is a photomicrograph of one embodiment of a laminate web of the present invention.

FIG. 8 is a photomicrograph showing in magnified detail a web of the present invention comprising nonwoven outer layers which has been extended to form apertures, and locally extended to produce regions 68 of fiber reorientation. As can be seen in FIG. 8, by locally extending portions of the web to a greater extent than others, the apertures formed thereby can be of different sizes. Thus, the region denoted generally as 70 in FIG. 8 has undergone more strain (i.e., local extension) than the region denoted by 72. Thus, the apertures in region 70 are larger than those in region 72, and the basis weight of the nonwoven web material in region 72 is less than the basis weight of the nonwoven web in region 70. In addition to the difference in basis weight due to localized strain differentials, the laminate web of the present invention can also exhibit distinct regions 68 of fiber reorientation. In these regions, the fibers have been reoriented from a generally random orientation to a predominant orientation in the direction of extension.

To make a web 10 as shown in FIG. 6, central layer 30 can be any of a great number of dissimilar materials. For example, if outer layers 20 and 40 are nonwoven webs having a relatively high elongation to break, central layer 30 can be paper, tissue paper, thermoplastic film, metal foil, closed or open cell foam, or any other material that has a relatively low elongation to break compared to the two outer layers. The outer layer materials may themselves be dissimilar, with the only constraint being that the central layer be relatively less extensible in the direction of extension to form apertures.

Additionally, more than one central layer 30 can be used with beneficial results. For example, a structure comprising a cellulosic tissue central web and a polymeric film central web between two nonwoven webs can produce an absorptive wiping article with one side being relatively more absorptive than the other. If the film layer is a three-dimensional formed film, the film side can provide added texture to the laminate which is beneficial in many wiping applications. Macroscopically-expanded, three-dimensional formed films suitable for use in the present invention include those described in commonly-assigned U.S. Pat. No. 3,929,135 issued to Thompson on Dec. 30, 1975, and U.S. Pat. No. 4,342,314 issued to Radel et al. on Aug. 3, 1982, both patents hereby incorporated herein by reference.

The (or "a") central layer can also be elastomeric, and can be an elastomeric macroscopically-expanded, vacuum-formed, three-dimensional formed film, such as described in commonly-assigned U.S. Ser. No. 08/816,106, entitled "Tear Resistant Porous Extensible Web" filed by Curro et al. on Mar. 14, 1997, and hereby incorporated herein by reference. Further, the (or "a") central layer can be a three-dimensional formed film having micro-apertures such as described in commonly-assigned U.S. Pat. Nos. 4,629,643 issued to Curro et al. on Dec. 16, 1986, and 4,609,518, issued to Curro et al. on Sep. 2, 1986, both of which are hereby incorporated herein by reference.

The (or "a") central layer can be a web material having a strainable network as disclosed in U.S. Pat. No. 5,518,801 issued to Chappell et al. on May 21, 1996, and hereby incorporated herein by reference. Such a web can be a structural elastic-like film (SELF) web, formed by, for example, embossing by mating plates or rolls.

The (or "a") central layer can be an absorbent open cell foam web material. Particularly suitable absorbent foams for high performance absorbent articles such as diapers have been made from High Internal Phase Emulsions (hereafter referred to as "HIPE"). See, for example, U.S. Pat. No. 5,260,345 (DesMarais et al), issued Nov. 9, 1993 and U.S. Pat. No. 5,268,224 (DesMarais et al), issued Dec. 7, 1993, hereby incorporated herein by reference. These absorbent HIPE foams provide desirable fluid handling properties, including: (a) relatively good wicking and fluid distribution characteristics to transport the imbibed urine or other body fluid away from the initial impingement zone and into other regions of the foam structure to allow for subsequent gushes of fluid to be accommodated; and (b) a relatively high storage capacity with a relatively high fluid capacity under load, i.e. under compressive forces.

The central layer 30 may comprise absorbent gelling materials. For example, supersorbers or hydrogel materials may provide for superior absorbency when the laminate web of the present invention is used as an absorbent wipe or an absorbent core in a disposable absorbent article. By "hydrogel" as used herein is meant an inorganic or organic compound capable of absorbing aqueous fluids and retaining them under moderate pressures. For good results the hydrogels should be water insoluble. Examples are inorganic materials such as silica gels and organic compounds such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinyl pyridine and the like.

One benefit of the laminate of the present invention is the ability to make a laminate structure of dissimilar materials without the use of adhesive for joining. Because the central layer of the laminate web 10 is penetrated by the protuberances of the calendaring roll at melt bond sites, it can comprise non-thermally-bondable materials. The plurality of melt bond sites 50 are sufficient to keep the component webs together in the laminate web, so that the laminate web behaves as a unitary web for processing integrity and use, without unwanted delamination. However, in some embodiments, and for certain materials, it may be beneficial to apply adhesive between at least two of the constituent layers.

The laminate web of the present invention, being bonded by a plurality of relatively closely spaced thermal bond sites (without the use of thermoplastic adhesives) can be beneficially used for durable articles. For example, a laminate web of the present invention comprising nonwoven web outer layers and having a clothlike feel and appearance, can be used in durable garments. Certain embodiments of the laminate web of the present invention can survive repeated washing and drying in household washing and drying equipment, depending on the component webs of the laminate, and the level of thermal bonding. Due to the knit-like or fabric-like look and feel of certain embodiments of the present invention, such durability can result in durable garment components such as interliners and the like. Alternatively, a woven fabric can comprise the outer layers to form a durable article.

METHOD OF MAKING

Figure 9:
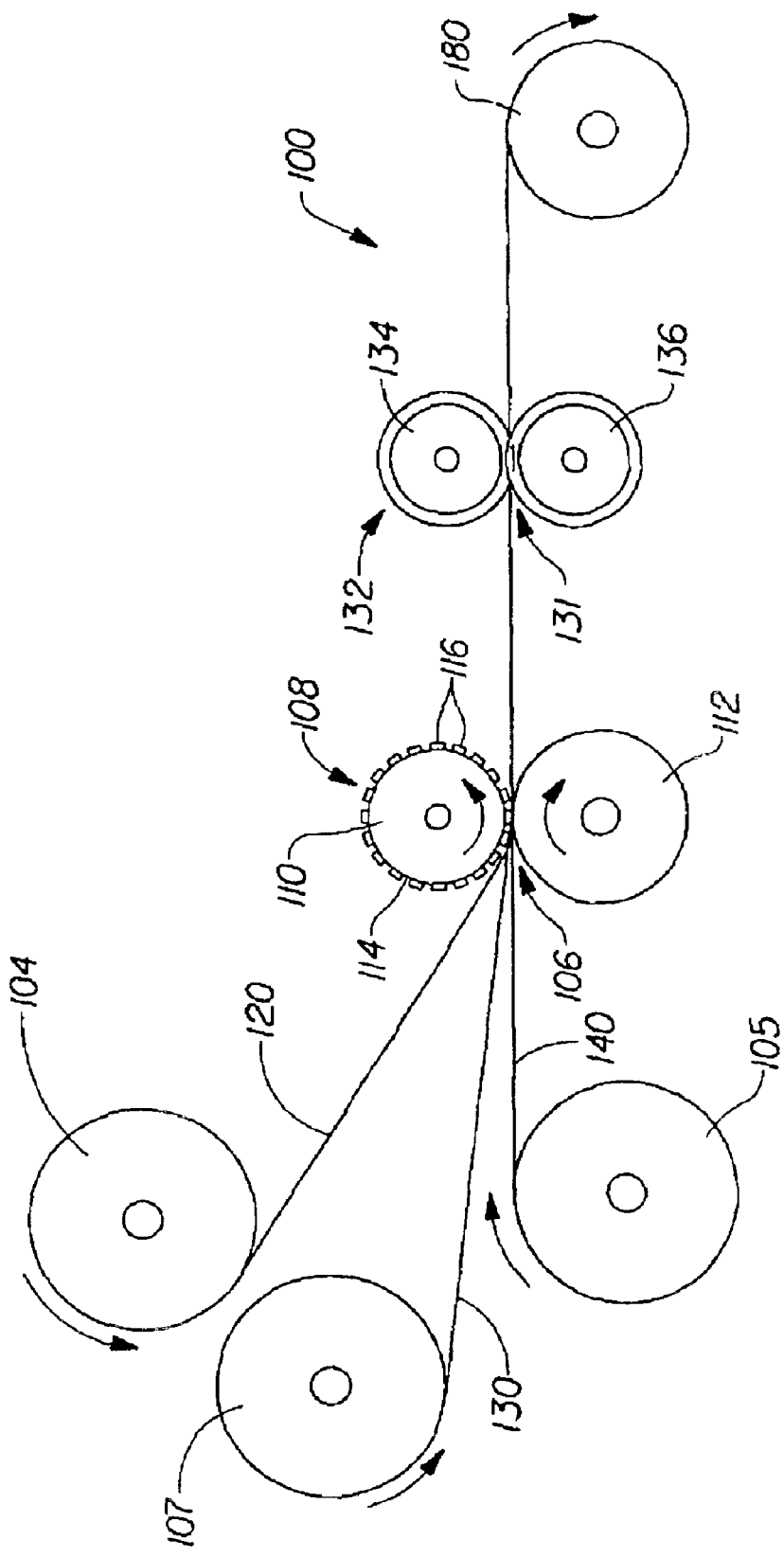
FIG. 9 is a schematic representation of a process for making a laminate web of the present invention.

Referring to FIG. 9 there is schematically illustrated at 100 a process making a laminate web of the present invention.

A first web 120 which can be a relatively extensible web, is unwound from a supply roll 104 and travels in a direction indicated by the arrows associated therewith as the supply roll 104 rotates in the direction indicated by the arrows associated therewith. Likewise a second web 140, which can be a relatively extensible web is unwound from supply roll 105. A central layer 130, which can be a relatively inextensible layer, is likewise drawn from supply roll 107. The three components (or more, if more than one central layer is used) pass through a nip 106 of the thermal point bond roller arrangement 108 formed by rollers 110 and 112.

In addition to thermoplastic nonwoven materials, either outer layer can comprise a polymeric film, for example a polyolefinic (e.g., PP or PE) thin film. If the entire outer layer is not uniformly thermoplastic, at least sufficient amounts to effect melt bonding must be thermoplastic. Conjugate fibers, such as bicomponent fibers can be used in the outer layers to facilitate thermal bonding of the outer layers. Either outer layer can comprise a formed film, such as a three-dimensional formed film having micro-apertures such as described in commonly-assigned U.S. Pat. Nos. 4,629,643 issued to Curro et al. on Dec. 16, 1986, and 4,609,518, issued to Curro et al. on Sep. 2, 1986, both of which are hereby incorporated herein by reference.

In a preferred embodiment, both outer layers comprise nonwoven materials, and may be the identical. The nonwoven material may be formed by known nonwoven extrusion processes, such as, for example, known meltblowing processes or known spunbonding processes, and passed directly through the nip 106 without first being bonded and/or stored on a supply roll. However, in a preferred embodiment, the nonwoven webs are themselves thermally point bonded (consolidated) webs commercially available on supply rolls. The thermal point bonds, which are typically in the form of a regular pattern of spaced-apart diamond shaped bond sites, are present in the nonwoven as purchased from a nonwoven vendor, and are to be distinguished in the web of the present invention from the bond sites 50 formed by the method of the present invention.

The nonwoven web outer layer(s) may be elastic, highly elastic or nonelastic. The nonwoven web may be any meltfusible web, including a spunbonded web, a meltblown web, or a bonded carded web. If the nonwoven web is a web of meltblown fibers, it may include meltblown microfibers. The nonwoven web may be made of fiber forming polymers such as, for example, polyolefins. Exemplary polyolefins include one or more of polypropylene, polyethylene, ethylene copolymers, propylene copolymers, and butene copolymers. The nonwoven web can have a basis weight between about 10 to about 60 grams per square meter (gsm), and more preferably about 15 to about 30 gsm.

The nonwoven web outer layers may themselves be a multilayer material having, for example, at least one layer of a spunbonded web joined to at least one layer of a meltblown web, a bonded carded web, or other suitable material. For example, the nonwoven web may be a multilayer web having a first layer of spunbonded polypropylene having a basis weight from about 0.2 to about 8 ounces per square yard, a layer of meltblown polypropylene having a basis weight from about 0.2 to about 4 ounces per square yard, and a second layer of spunbonded polypropylene having a basis weight from about 0.2 to about 8 ounces per square yard. Alternatively, the nonwoven web may be a single layer of material, such as, for example, a spunbonded web having a basis weight from about 0.2 to about 10 ounces per square yard or a meltblown web having a basis weight from about 0.2 to about 8 ounces per square yard.

The nonwoven web outer layers may also be a composite made up of a mixture of two or more different fibers or a mixture of fibers and particles. Such mixtures may be formed by adding fibers and/or particulates to the gas stream in which meltblown fibers or spunbond fibers are carried so that an intimate entangled co-mingling of fibers and other materials, e.g., wood pulp, staple fibers and particles occurs prior to collection of the fibers.

Prior to processing by the method of the present invention, the nonwoven web outer cover of fibers can be joined by bonding to form a coherent web structure. Suitable bonding techniques include, but are not limited to, chemical bonding, thermobonding, such as point calendering, hydroentangling, and needling.

Figure 10:
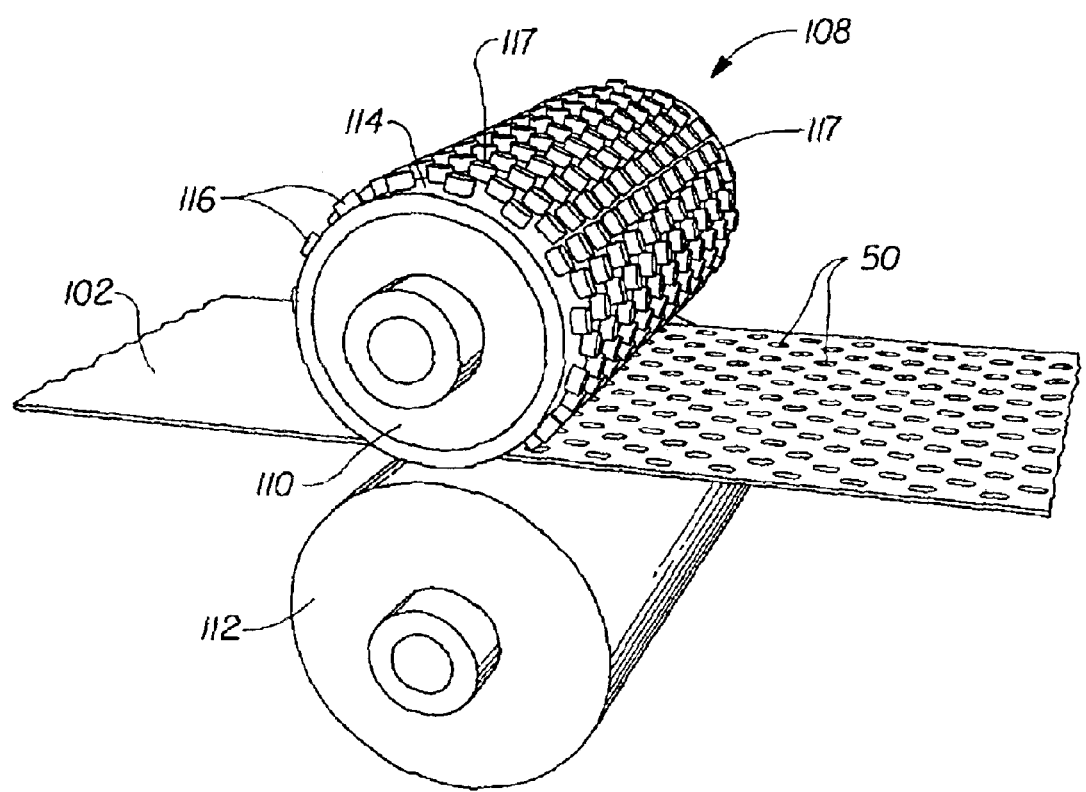
FIG. 10 is a perspective view of a melt bond calendaring apparatus.
Figure 11:
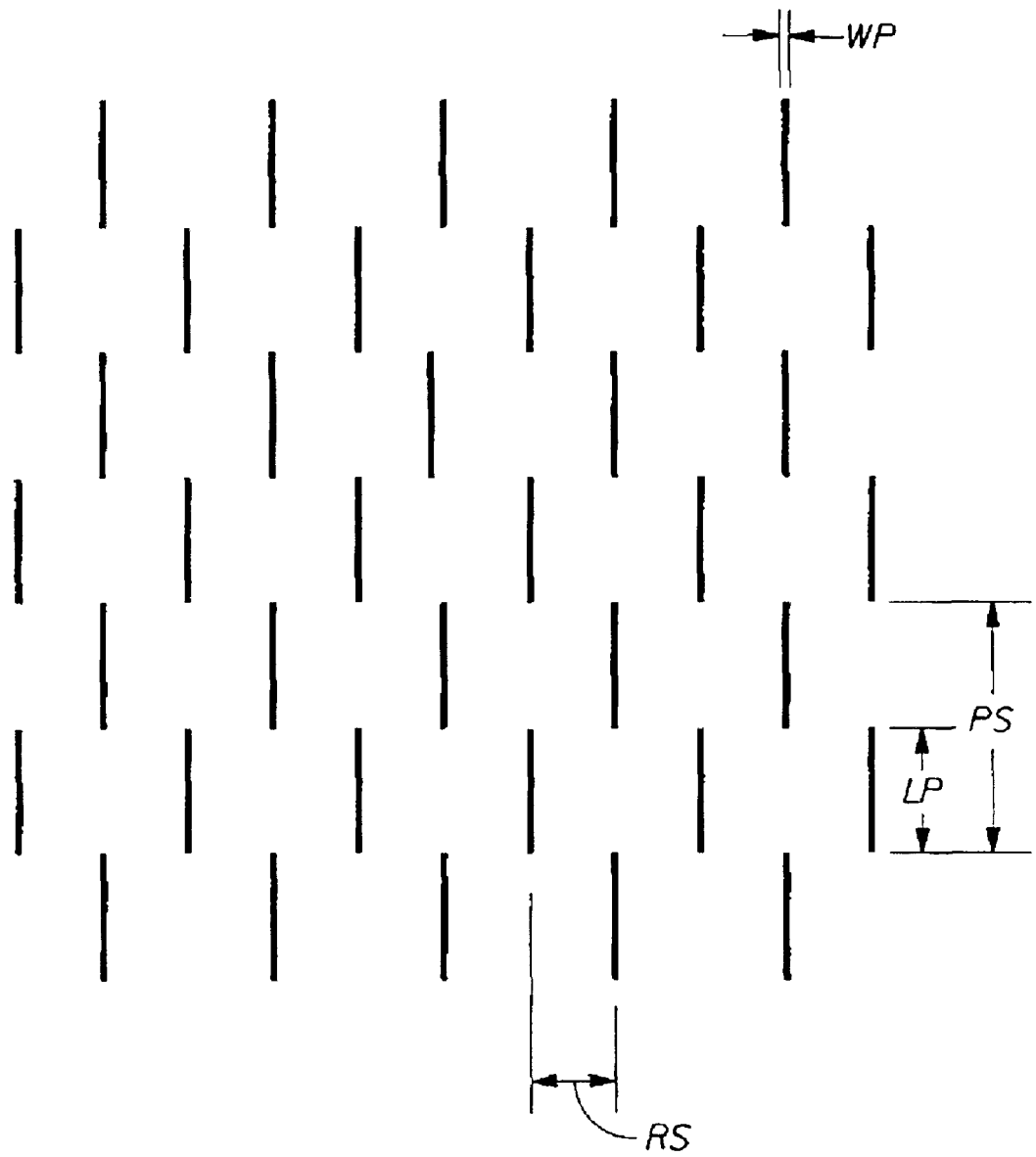
FIG. 11 is a schematic representation of a pattern for the protuberances of the calendaring roll.

Referring to FIGS. 9 and 10, the nonwoven thermal bond roller arrangement 108 preferably comprises a patterned calendar roller 110 and a smooth anvil roller 112. One or both of the patterned calendar roller 110 and the smooth anvil roller 112 may be heated and the temperature of either roller and the pressure between the two rollers may be adjusted by well known means to provide the desired temperature, if any, and pressure to concurrently displace central layer 30 at melt bond sites, and melt bond the two outer layers together at a plurality of bond sites.

The patterned calendar roller 110 is configured to have a circular cylindrical surface 114, and a plurality of protuberances or pattern elements 116 which extend outwardly from surface 114. The protuberances 116 are disposed in a predetermined pattern with each protuberance 116 being configured and disposed to displace central layer 30 at melt bond sites, and melt bond the two outer layers together at a plurality of locations. One pattern of protuberances is shown schematically in FIG. 11. As shown, the protuberances 116 have a relatively small width, WP, which can be between about 0.003 inches and 0.020 inches, but in a preferred embodiment is about 0.010 inches. Protuberances can have a length, LP, of between about 0.030 inches and about 0.200 inches, and in a preferred embodiment has a length of about 0.100 inches. In a preferred embodiment, the protuberances have an aspect ratio (LP/WP) of 10. The pattern shown is a regular repeating pattern of staggered protuberances, generally in rows, each separated by a row spacing, RS, of about between about 0.010 inches and about 0.200 inches. In a preferred embodiment, row spacing RS is about 0.060 inches. The protuberances can be spaced apart within a row by a protuberance spacing, PS, generally equal to the protuberance length, LP. But the spacing and pattern can be varied in any way depending on the end product desired.

As shown in FIG. 10, patterned calendar roller 110 can have a repeating pattern of protuberances 116 which extend about the entire circumference of surface 114. Alternatively, the protuberances 116 may extend around a portion, or portions of the circumference of surface 114. Likewise, the protuberances 116 may be in a non-repeating pattern, or in a repeating pattern of randomly oriented protuberances. Of course, if randomly oriented, the opening of the resulting bond sites into apertures will also be somewhat random, depending on the orientation of the bond site with respect to the direction of tension, as discussed below. For example, if the web is tensioned in the cross-direction (CD) direction only, then the bond sites 50 having a longitudinal axis 1 with a vector component in the machine direction (MD) will open into an aperture, at least to the degree of the magnitude of such a vector component.

The protuberances 116 are preferably truncated conical shapes which extend radially outwardly from surface 114 and which have rectangular or somewhat elliptical distal end surfaces 117. Although it is not intended to thereby limit the scope of the present invention to protuberances of only this configuration, it is currently believed that the high aspect ratio of the melt bond site 50 is only achievable if the protuberances likewise have a narrow width and a high aspect ratio at the distal end surfaces 117, as shown above with reference to FIG. 11. The roller 110 is preferably finished so that all of the end surfaces 117 lie in an imaginary right circular cylinder which is coaxial with respect to the axis of rotation of roller 110.

The height of the protuberances should be selected according to the thickness of the laminate being bonded. In general, the height dimension should be greater than the maximum thickness of the laminate web during the calendaring process, so that adequate bonding occurs at the bond sites, and only at the bond sites.

Anvil roller 112, is preferably a smooth surfaced, right circular cylinder of steel.

After passing through nip 106, the three (or more) component webs 120, 130, and 140, shown together as web 102 in FIG. 10, have been formed into laminate web 10. At this point in the process, the outer layers are thermally bonded to each other and unapertured, as shown in FIGS. 1 and 2. Central layers(s) 30, from web 130, is apertured, having been displaced by protuberances 116 in nip 106. Depending on the central layer(s) used, it (they) may or may not participate in the bonding about the periphery of the bond sites. In some instances, particularly for non-thermoplastic, non-fibrous materials, the central layer may not be involved in the bonding of the outer layers at all. However, for thermoplastic materials and fibrous materials, some involvement of the central layer(s) is observed.

The laminate web 10 may be further processed to form apertures in the whole laminate web (or portions thereof) by extending portions of the web in a direction orthogonal to the axis 1 of bond sites 50. As shown in FIGS. 9 and 10, the axis 1 is generally parallel to the machine direction MD of the web being processed. Therefore, extension in the cross-direction CD at the bonded portions causes the bond sites 50 to rupture and open to form apertures in the web.

One method for forming apertures across the web is to pass the web through nip 131 formed by incremental stretching system 132 employing opposed pressure applicators 134 and 136 having three-dimensional surfaces which at least to a degree are complementary to one another. Stretching of the laminate web may be accomplished by other methods known in the art, including tentoring, or even by hand. However, to achieve even strain levels across the web, and especially if localized strain differential are desired, the incremental stretching system disclosed herein is preferred.

Figure 12:
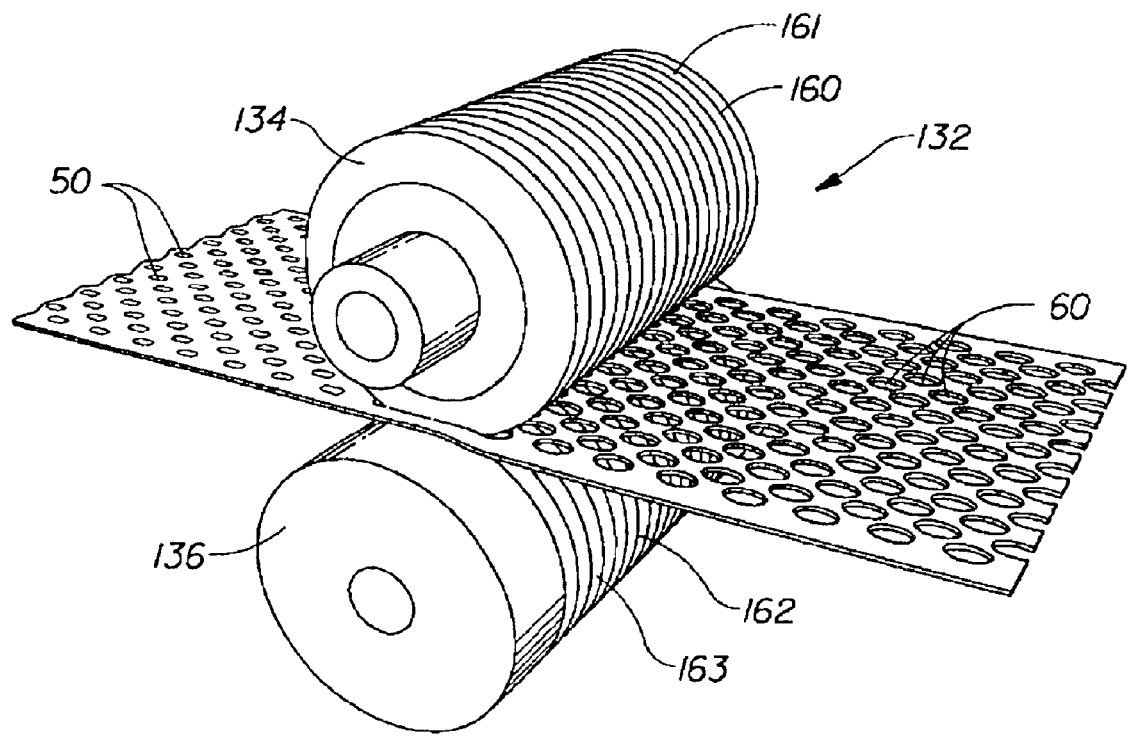
FIG. 12 is a perspective view of an apparatus for stretching a laminate of the present invention to form apertures therein.
Figure 13:
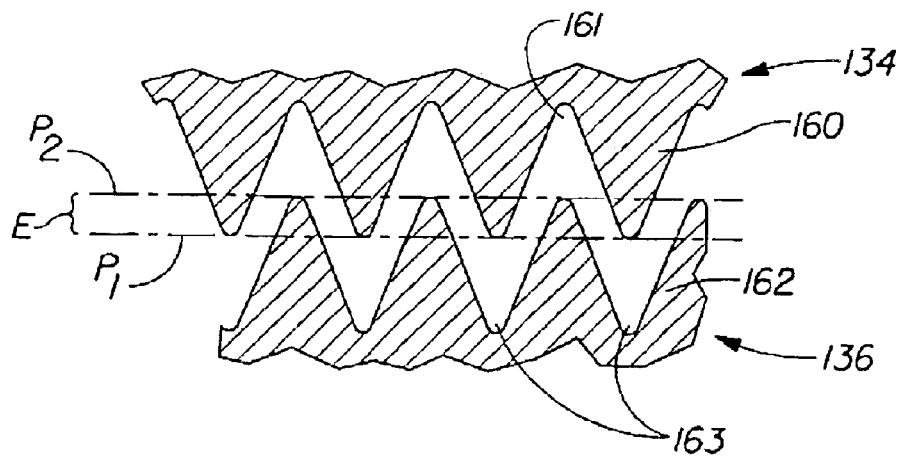
FIG. 13 is a cross-sectional view of a portion of the mating portions of the apparatus shown in FIG. 12.

Referring now to FIG. 12, there is shown a fragmentary enlarged view of the incremental stretching system 132 comprising incremental stretching rollers 134 and 136. The incremental stretching roller 134 includes a plurality of teeth 160 and corresponding grooves 161 which extend about the entire circumference of roller 134. Incremental stretching roller 136 includes a plurality of teeth 162 and a plurality of corresponding grooves 163. The teeth 160 on roller 134 intermesh with or engage the grooves 163 on roller 136, while the teeth 162 on roller 136 intermesh with or engage the grooves 161 on roller 134. The teeth of each roller are generally triangular-shaped, as shown in FIG. 13. The apex of the teeth may be slightly rounded, if desired for certain effects in the finished web.

FIG. 13, shows a portion of the intermeshing of the teeth 160 and 162 of rollers 134 and 136, respectively. The term "pitch" as used herein, refers to the distance between the apexes of adjacent teeth. The pitch can be between about 0.02 to about 0.30 inches, and is preferably between about 0.05 and about 0.15 inches. The height (or depth) of the teeth is measured from the base of the tooth to the apex of the tooth, and is preferably equal for all teeth. The height of the teeth can be between about 0.10 inches and 0.90 inches, and is preferably about 0.25 inches and 0.50 inches.

The teeth 160 in one roll can be offset by one-half the pitch from the teeth 162 in the other roll, such that the teeth of one roll (e.g., teeth 160) mesh in the valley (e.g., valley 163) between teeth in the mating roll. The offset permits intermeshing of the two rollers when the rollers are "engaged" or in an intermeshing, operative position relative to one another. In a preferred embodiment, the teeth of the respective rollers are only partially intermeshing. The degree to which the teeth on the opposing rolls intermesh is referred to herein as the "depth of engagement" or "DOE" of the teeth. As shown in FIG. 13, the DOE, E, is the distance between a position designated by plane P1 where the apexes of the teeth on the respective rolls are in the same plane (0% engagement) to a position designated by plane P2 where the apexes of the teeth of one roll extend inward beyond the plane P1 toward the valley on the opposing roll. The optimum or effective DOE for particular laminate webs is dependent upon the height and the pitch of the teeth and the materials of the web.

In other embodiments the teeth of the mating rolls need not be aligned with the valleys of the opposing rolls. That is, the teeth may be out of phase with the valleys to some degree, ranging from slightly offset to greatly offset.

As the laminate web 10 having melt bonded locations 50 passes through the incremental stretching system 132 the laminate web 10 can be subjected to tensioning in the CD or cross-machine direction causing the laminate web 10 to be extended in the CD direction. Alternatively, or additionally, the laminate web 10 may be tensioned in the MD (machine direction). The tensioning force placed on the laminate web 10 can be adjusted (e.g., by adjusting DOE) such that it causes the melt bonded locations 50 to separate or rupture creating a plurality of apertures 60 coincident with the melt bonded locations 50 in the laminate web 10. However, portions of the melt bonds of the laminate web 10 remain, as indicated by portions 62 in FIG. 4, thereby maintaining the laminate web in a coherent, unitary web condition even after the melt bonded locations rupture.

After being subjected to the tensioning force applied by the incremental stretching system 132, the laminate web 10 includes a plurality of apertures 60 which are coincident with the melt bonded regions 50 of the laminate web. As mentioned, a portion of the circumferential edges of apertures 60 include remnants 62 of the melt bonded locations 60. It is believed that the remnants 60 help to resist further tearing or delamination of the laminate web. Remnants 62 may also contain portions of central layer 30, to the extent that the central layer is involved in the bonding.

Figure 14:
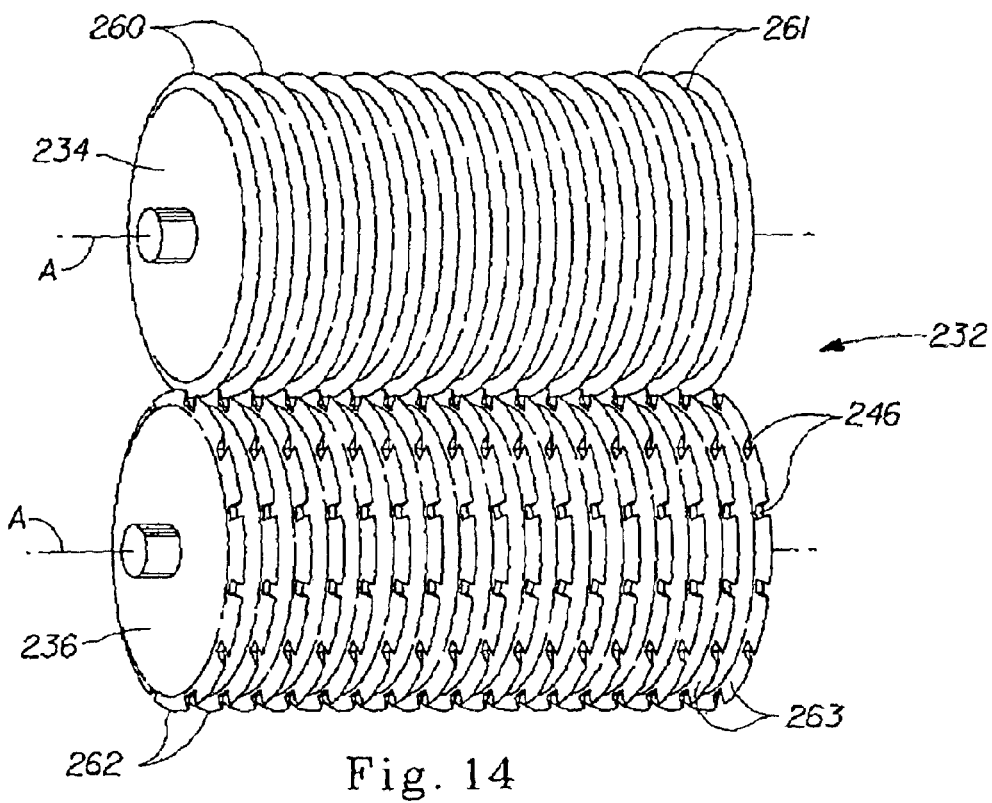
FIG. 14 is a perspective view of an alternative apparatus for stretching a laminate of the present invention in the cross-machine direction to form apertures therein.

Instead of two substantially identical rolls 134 and 136, one or both rolls can be modified to produce extension and additional patterning. For example, one or both rolls can be modified to have cut into the teeth several evenly-spaced thin channels 246 on the surface of the roll, as shown on roll 236 in FIG. 14. In FIG. 14 there is shown an enlarged view of an alternative incremental stretching system 232 comprising incremental stretching rollers 234 and 236. The incremental stretching roller 234 includes a plurality of teeth 260 and corresponding grooves 261 which extend about the entire circumference of roller 234. Incremental stretching roller 236 includes a plurality of teeth 262 and a plurality of corresponding grooves 263. The teeth 260 on roller 234 intermesh with or engage the grooves 263 on roller 236, while the teeth 262 on roller 236 intermesh with or engage the grooves 261 on roller 234. The teeth on one or both rollers can have channels 246 formed, such as by machining, such that regions of undeformed laminate web material may remain after stretching. A suitable pattern roll is described in U.S. Pat. No. 5,518,801, issued May 21, 1996, in the name of Chappell, et al., the disclosure of which is incorporated herein by reference.

Figure 15:
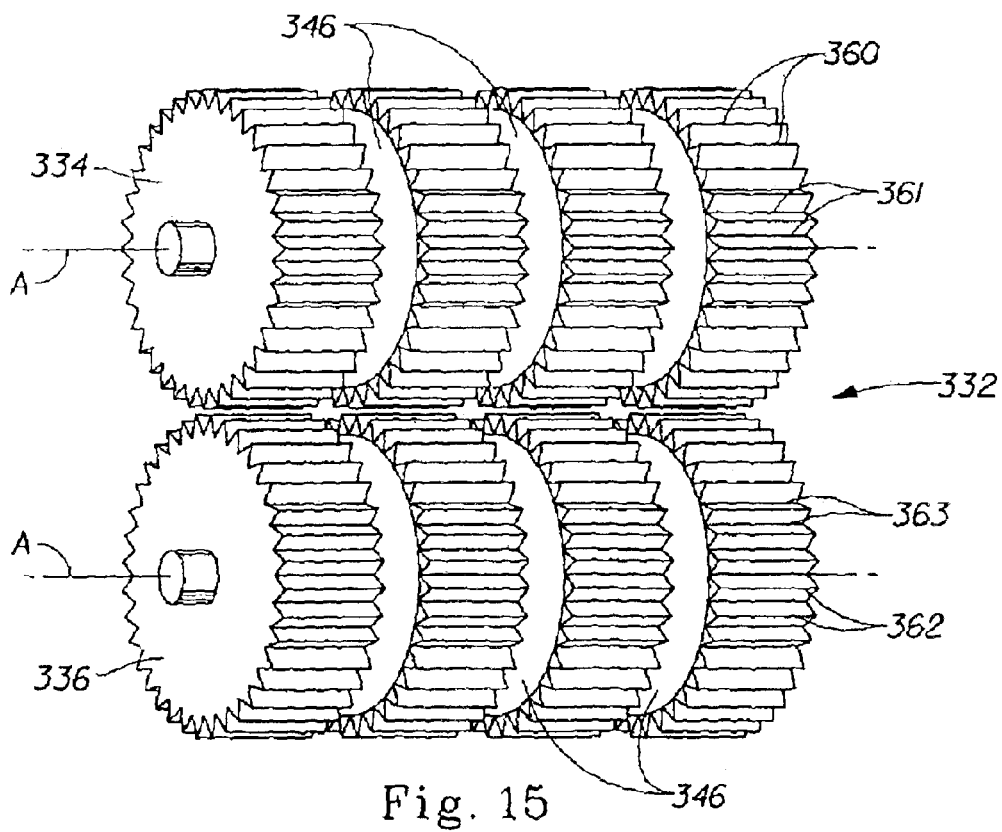
FIG. 15 is a perspective view of another alternative apparatus for stretching a laminate of the present invention in the machine direction to form apertures therein.

Likewise, the incremental stretching can be by mating rolls oriented as shown in FIG. 15. Such rolls comprise a series of ridges 360, 362, and valleys, 361, 363 that run parallel to the axis, A, of the roll, either 334 or 336, respectively. The ridges form a plurality of triangular-shaped teeth on the surface of the roll. Either or both rolls may also have a series of spaced-apart channels 346 that are oriented around the circumference of the cylindrical roll. Rolls as shown are effective in incrementally stretching a laminate web 10 in the machine direction, MD if the axis 1 of bond sites 50 is oriented generally parallel to the cross-machine, CD direction of the web as its being processed.

Figure 16:
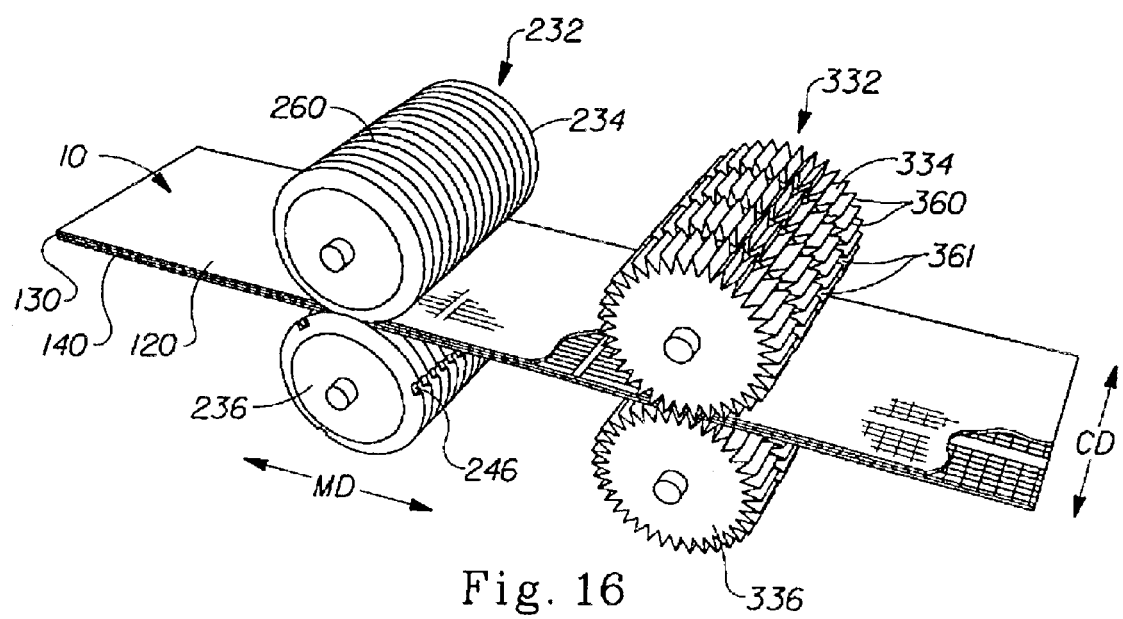
FIG. 16 is a perspective representation of an apparatus for stretching a laminate of the present invention in both the cross-machine and machine directions to form apertures therein.

In one embodiment, the method of the present invention can comprise both CD and MD incremental stretching. As shown in FIG. 16, two pairs of incremental stretching rolls can be used in line, such that one pair (232, which, as shown in FIG. 16 includes a series of spaced-apart channels 246) performs CD stretching, and another pair, 332 performs MD stretching. By this method many interesting fabric-like textures can be made. The resulting hand and visual appearance make such fabric-like webs ideal for use in articles benefiting from a fabric-like look and feel. For example, if a central layer 30 comprises a material having less elongation to break than either outer layer, and is stretched to failure in both the CD and MD directions by the method described herein, the resulting laminate web 10 exhibits "islands" of central layer material. The islands are discrete, non-continuous portions of central layer, and give the laminate web 10 a decidedly fabric-like look and feel. In this manner, if a metal foil is used as a central layer 30 between two relatively translucent materials, such as low basis weight nonwovens, the resulting laminate web 10 resembles a sequined fabric.

The use of rather brittle, or relatively still materials can be used as a central layer 30 with beneficial results when the laminate web is incrementally stretched as described herein. For example, thin ceramic materials having a relatively high stiffness can be used as central layer 30 in a laminate web 10 that is relatively highly flexible in at least one direction, depending on the direction of stretch. Therefore, if the web is incrementally stretched in the CD direction, the laminate web will be flexible about an axis parallel with the MD direction, and vice-versa. If the web is incrementally stretched in both directions, then the resulting laminate web 10 will be relatively highly flexible about two axes, and, depending on the size of the discrete "islands" of central layer produced, approaches the overall flexibility of the two outer layers.

EXAMPLES

The following examples are shown in Table 1 as exemplary of the claimed invention. Because the choice of outer and inner layers and combinations is virtually infinite, the examples shown are meant to be illustrative of possible structures, and are not meant to be limiting to any particular material or structure. In particular, the examples shown are limited to currently preferred structures comprising nonwoven webs as the outer layers.

In Table 1 various combinations of materials are shown. The layers are numbered in order of structural proximity from one outer layer to the other. Therefore, layer 1 is always an outer layer, and the last numbered layer is likewise an outer layer.

For all the samples shown, the calendaring line speed was 100 feet per minute, but the line speed is not considered critical to the operation of the method. The calendaring pressure was 700 psig for all the samples, but the pressure can be varied as desired as long as bonding is achieved between the outer layers.

To form apertured embodiments of the samples below, the thermally bonded laminate was processed by the incremental stretching process as described above with reference to FIG. 12. For these samples a "Pitch" and depth of engagement ("DOE") are shown.

Clopay PE films were obtained from Clopay, Cincinnati, Ohio. These thin (about 0.001" thick) films are a soft and deformable polyethylene type, often used as fluid barrier materials for absorbent products.

Tredegar elastomeric formed films were obtained from Tredegar Film Products, Terre Haute, Ind. By "form ed film" is meant a macroscopically-expanded three-dimensional plastic web comprising a continuum of capillary networks originating in and extending from one surface of the web and terminating in the form of apertures in the opposite surface thereof. Such a formed film is disclosed in commonly assigned U.S. Pat. No. 4,342,314 issued to Radel et al. on Aug. 3, 1982. Elastomeric formed films are an improvement in the aforementioned Radel et al. web as disclosed in the above-mentioned commonly assigned, copending U.S. patent application Ser. No. 08/816,106 entitled Tear Resistant Porous Extensible Web, filed Mar. 14, 1997 in the name of Curro et al. Curro '106 discloses elasticized polymeric webs generally in accordance with the aforementioned Radel et al. patent that may be produced from elastomeric materials known in the art, and may be laminates of polymeric materials. Laminates of this type can be prepared by coextrusion of elastomeric materials and less elastic skin layers and may be used in the body hugging portions of absorbent garments, such as the waistband portions and leg cuffs.

High internal phase emulsion open cell foam materials can be made generally in accordance with the teachings of the above mentioned U.S. Pat. No. 5,260,345 and U.S. Pat. No. 5,268,224.

BBA and Corovin/BBA nonwovens were obtained form BBA, Greenville, S.C.

BOUNTY® paper towels were obtained from The Procter & Gamble Co., Cincinnati, Ohio.

REYNOLD'S metal foil products were obtained from Reynold's Metal Products company.

3M products were obtained from 3M, Minneapolis, Minn.

For the materials shown below, the basis weight is expressed in grams per square meter (gsm). Low density polyethylene is denoted "LDPE"; polypropylene is denoted as "PP"; and polyethylene is denoted as "PE". Spunbond is denoted as "SB".

TABLE 1

Examples of Laminate Webs of the Present Invention

| Example No. | Layer 1 | Layer 2 | Layer 3 | Layer 4 | Layer 5 | Roller Temp. Anvil/ Pattern (deg. F.) | Pitch/ DOE (inches) |
| --- | --- | --- | --- | --- | --- | --- | --- |
| 1 | 30 gsm LDPE SB nonwoven from Corovin/BBA | 42 gsm BOUNTY® Paper Towel | 30 gsm LDPE SB nonwoven from Corovin/BBA | | | 250/270 | |
| 2 | 30 gsm LDPE SB nonwoven from Corovin/BBA | 42 gsm BOUNTY® Paper Towel | 42 gsm BOUNTY® Paper Towel | 30 gsm LDPE SB nonwoven from Corovin/BBA | | 250/270 | 0.200/ 0.300 |
| 3 | 30 gsm LDPE SB nonwoven from Corovin/BBA | 42 gsm BOUNTY® Paper Towel | 30 gsm LDPE SB nonwoven from Corovin/BBA | | | 250/270 | 0.060/ 0.850 |

TABLE 1-continued

Examples of Laminate Webs of the Present Invention

| Example No. | Layer 1 | Layer 2 | Layer 3 | Layer 4 | Layer 5 | Roller Temp. Anvil/ Pattern (deg. F.) | Pitch/ DOE (inches) |
|---|---|---|---|---|---|---|---|
| 4 | 80/20 (PE/PP) 30 gsm SB nonwoven from BBA | 23 gsm PE film from Clopay | 50/50 (PE/PP) 30 gsm SB nonwoven from BBA | | | 275/295 | |
| 5 | 80/20 (PE/PP) 30 gsm SB nonwoven from BBA | 23 gsm PE film from Clopay | 50/50 (PE/PP) 30 gsm SB nonwoven from BBA | | | 275/295 | 0.200/ 0.300 |
| 6 | 80/20 (PE/PP) 30 gsm SB nonwoven from BBA | 42 gsm BOUNTY ® Paper Towel | 23 gsm PE film from Clopay | 50/50 (PE/PP) 30 gsm SB nonwoven from BBA | | 275/295 | |
| 7 | 80/20 (PE/PP) 30 gsm SB nonwoven from BBA | 42 gsm BOUNTY ® Paper Towel | 23 gsm PE film from Clopay | 50/50 (PE/PP) 30 gsm SB nonwoven from BBA | | 275/295 | 0.200/ 0.300 |
| 8 | 30 gsm LDPE SB nonwoven from Corovin/BBA | M77 spray adhesive from 3M approx. 13 gsm | REYNOLDS ® 65 gsm aluminum foil | M77 spray adhesive from 3M approx. 13 gsm | 30 gsm LDPE SB nonwoven from Corovin/BBA | 275/295 | 0.060/ 0.850 |
| 9 | 30 gsm LDPE SB nonwoven from Corovin/BBA | 88 gsm elastomeric formed film from Tredegar | 42 gsm BOUNTY ® Paper Towel | 30 gsm LDPE SB nonwoven from Corovin/BBA | | 250/270 | 0.200/ 0.300 |
| 10 | 30 gsm LDPE SB nonwoven from Corovin/BBA | Spray hot melt adhesive from Ato-Findley approx. 12 gsm | 62 gsm High Internal Phase Emulsion open cell foam | Spray hot melt adhesive from Ato-Findley approx. 12 gsm | 30 gsm LDPE SB nonwoven from Corovin/BBA | 250/270 | 0.200/ 0.300 |
| 11 | 27 gsm high elongation carded PP nonwoven from BBA | 42 gsm BOUNTY ® Paper Towel | 60 gsm laminate of 80/20 50/50 (PE/PP) nonwoven from BBA | | | 295/350 | 0.060/ 0.110 |

The laminate webs of the present invention may be utilized in many varied applications. For example, the relatively low cost of nonwoven, paper and film materials makes the laminates ideally suited for disposable articles.

The laminates of the present invention can also be useful in absorbent medical applications such as medical gauze or absorbent surgical drape. A medical gauze can be made by forming a laminate from a first outer layer of nonwoven material such as 30 gsm LDPE SB nonwoven from Corovin/BBA, an inner layer comprising a 42 gsm Bounty™ paper towel and a second outer nonwoven of 30 gsm LDPE SB. Apertures within the laminate would provide a path for air to flow to the wound to facilitate healing, while the inner Bounty™ layer would pull fluid away from the gauze surface to help keep the wound clean. The same laminate as described above would also be useful as an absorbent surgical drape. The nonwoven outer layers would prevent cellulose fibers from the absorbent Bounty™ inner layer from contaminating the incision area during a surgical procedure. In both the medical gauze and surgical drape examples, the outer nonwoven layers could be treated to be hydrophobic, hydrophilic or to have different surface energies on each side. In the case where one nonwoven outer layer is more hydrophilic than the other nonwoven outer layer, the resulting medical gauze or surgical drape would have one side that is more likely to absorb the fluid and an opposite side that is more likely to stay dry.

Laminates of the present invention can be useful for bedding applications, such as blankets, sheets and pillowcases. A blanket can be formed from a first outer layer of nonwoven material such as 30 gsm LDPE SB nonwoven from Corovin/BBA, one or more inner layers comprising a macroscopically formed film such as Always Dri-weave™ Topsheet and a second outer nonwoven of 30 gsm LDPE SB. The formed film in the center provides the required bulk to the blanket, while the outer nonwovens provide the required softness. Apertured versions of this laminate resemble the look and feel of a loose knit. Alternate stretching process conditions can be used to form smaller apertures or a non-apertured version of the laminate that may be more suitable for sheets and pillowcases. The inner layer can be replaced with a 23 gsm PE flat film from Clopay to reduce bulk for the sheet and pillowcase applications. The outer nonwovens may be formed from fibers with a high melt temperature, such as Polyester or Nylon, for bedding applications that must be able to be washed and dried several times throughout the life of the product.

Other suitable uses for laminates of the present invention are for use as flexible carrying implement, such as a laundry bag, a swim/beach bag, a garment bag or a purse. The laminate can be formed from a first outer layer of 30 gsm PET/PET Bicomponent carded IR bonded nonwoven from HDK Industries, an inner layer that could be any number of nonwovens, films, foils or knitted/woven materials, and a second outer nonwoven of 30 gsm PET/PET Bicomponent. The outer nonwovens provide the required hand feel and durability, while the inner layer provides additional strength and decorative aesthetics. The layers of the laminate may be, but are generally not absorbent, so as to serve as a barrier between the contents in the bag and the outside environment. The laminate may or may not be apertured. If the laminate is apertured, the aperture size and spacing may vary from very open (i.e., for a laundry bag) to very closed (i.e., for a purse).

Alternative uses of the laminates of the present invention are useful for absorbent kitchen and bathroom implements such as a dish towel, a scrub pad, a sponge, a bath/hand towel or a bath rug. In the cases of the dish towel, bath/hand towel and the bath rug, the laminate can be formed from a first outer layer of a 30 gsm 70% Bicomponent (PE/PP)/30% Viscose Rayon carded TPB nonwoven from PGI, one or more inner layers of 42 gsm Bounty™ paper towel and a second outer nonwoven of 30 gsm 70/30 Bico./Rayon carded TPB. The laminate may or may not be apertured, and the outer nonwovens may be formed with synthetic fibers with a high melt temperature, such as Polyester or Nylon, for towels and rugs that are meant to be more durable than disposable. In the cases of a scrub pad or sponge, the laminate of the present invention may serve as the entire implement or it may be a component of the implement, for example the scrubbing side or the absorbent side. A laminate for a sponge may be formed from a first outer layer of a 30 gsm 70% Bicomponent (PE/PP)/30% Viscose Rayon carded TPB nonwoven from PGI, an inner layer of 85 gsm high loft batting (30% PET/70% PE/PET Bico.) and a second outer nonwoven of 30 gsm 70/30 Bico./Rayon carded TPB. The laminate may be non-apertured, or it may have apertures to promote the formation of suds in soapy water. The laminate may have surfactant impregnated within or coated onto the surface of any of the layers. The inner batting may be sided (i.e., printed PE dots on one side) such that the resultant laminate also has sides suited for different tasks (i.e., scrubbing vs. wiping).

Tablecloths, placemats and the like are other suitable kitchen implements for laminates of the present invention. The laminate can be formed from a first outer layer of nonwoven material such as 30 gsm LDPE SB nonwoven from Corovin/BBA, an inner layer comprising a 42 gsm Bounty™ paper towel and a second outer layer of 23 gsm PE film from Clopay. The laminate may be non-apertured to maximize protection of the table surface or apertured to form an aesthetically pleasing pattern. The outer layers need not be different (i.e., both nonwovens or both films) and the inner layer need not be absorbent (i.e., could be any number of nonwovens, films, foils, foams or knitted/woven materials). All layers may be formed with higher melt point materials, such as Polyester or Nylon, if the article must be washed and dried several times throughout the course of its life.

Laminates of the present invention can also be useful as decorative coverings for gifts (wrap, bags, bows, etc.) and home accent items (lamp shades, picture frames, photo albums, etc.) The laminate may be formed from a first outer layer of nonwoven such as 30 gsm PET/PET Bicomponent carded IR bonded nonwoven from HDK Industries, an inner layer comprising any number of papers (including commercial gift wrap paper), nonwovens, films, foils, foams or knitted/woven materials and a second outer non-woven of 30 gsm PET/PET Bicomponent. The laminate may be non-apertured or apertured to form an aesthetically pleasing pattern. Alternately, the outer layers can be a knitted/woven material (i.e., an open weave PET athletic mesh) that is thermally bonded together through an inner layer to form a laminate of the present invention.

A laminate web of the present invention can find use in articles for the pet industry such as pet placemats, pet absorbent liners and coverings for pet beds. The laminate may be formed from a first outer layer of nonwoven such as 30 gsm PET/PET Bicomponent carded IR bonded nonwoven from HDK Industries, an inner layer comprising one or more layers of 42 gsm Bounty™ paper towel and a second outer nonwoven of 30 gsm PET/PET Bicomponent. The laminate may be non-apertured or apertured. Either of the outer nonwoven layers or the inner paper layer may be printed/dyed to impart color or design to the laminate.

Disposable bed pads are another suitable bedding application for the laminates of the present invention. The laminate may be formed from a first outer layer of nonwoven material such as 30 gsm LDPE SB nonwoven from Corovin/BBA, an inner layer comprising a 42 gsm Bounty™ paper towel and a second outer layer of 23 gsm PE flat film from Clopay. The flat film would be placed against the bed, while the soft nonwoven side would be placed against the skin. The laminate would most likely be non-apertured to prevent fluid leak though, but could contain small apertures to promote air and moisture permeability. Alternately, a microporous flat film could be used to impart breathable characteristics to the non-apertured laminate.

The laminates of the present invention can also be useful in construction/industrial applications such as a wall reinforcement/patch, landfill liners and safety fencing/netting. This laminate may be formed from a first outer layer of nonwoven material such as 30 gsm PET/PET Bicomponent carded IR bonded nonwoven from HDK Industries, an inner layer of TYVEK® from DuPont, and a second outer nonwoven of 30 gsm PET/PET Bicomponent. The laminate may be non-apertured or apertured. The result is a soft, flexible laminate with the known strength characteristics of TYVEK®.

Signage materials are also uses of the laminates of the present invention. The laminate may be formed from a first outer layer of nonwoven material such as 30 gsm LDPE SB nonwoven from Corovin/BBA, an inner layer comprising a 42 gsm Bounty™ paper towel and a second outer nonwoven of 30 gsm LDPE SB. The inner layer of Bounty™ can be printed on one or both sides with the desired text, designs and logo that can be seen through the outer nonwoven layers. The outer nonwoven layers also protect the inner Bounty™ paper layer and give it additional strength. The laminate may be non-apertured or apertured. However, an apertured version of the laminate gives the additional advantage of providing a path for wind/air flow such that the sign is not damaged by environmental wind conditions.

The laminates of the present invention are also useful as flexible, soft coverings over rigid items such as baby care accessories (wet wipe containers, bottle caps, etc.) and office furnishings (arm rests, keyboard wrist supports, etc.) The laminate may be formed from a first outer layer of nonwoven material such as 30 gsm LDPE SB nonwoven from Corovin/BBA, one or more inner layers comprising a macroscopically formed film such as Always Dri-weave™ Topsheet and a second outer nonwoven of 30 gsm LDPE SB. The formed film layer(s) in the center provides the required bulk and compression characteristics, while the outer layers provide the required softness for skin contact, baby teething, etc. Alternately, the inner layer can comprise a foam material for additional softness and compressibility.

The laminates of the present invention can find use as fabric backings for carpets and rigid office furniture, such as chairs. The laminates may be formed from a first outer nonwoven such as 30 gsm PET/PET Bicomponent carded IR bonded nonwoven from HDK Industries, an inner layer of TYVEK® from DuPont, and a second outer nonwoven of 30 gsm PET/PET Bicomponent. Advantages of the laminate include inexpensive porosity via the (optional) apertures, and a strong yet flexible web well suited for industrial backing. Alternately, one or both of the outer nonwovens can be replaced with a tacky film to impart slip resistance characteristics, or the inner layer can be replaced with an elastomer such as an 88 gsm elastomeric formed film from Tredegar and/or a foam to impart stretch/recovery and/or compressibility characteristics to the web.

Laminates of the present invention could also be used as fabrics for clothing with a unique combination of properties. One example is breathable yet impervious to fluid and flexible fabrics that can be custom painted, drawn, or printed on. A breathable yet fluid impervious fabric laminate may be formed from a first outer nonwoven such as 30 gsm PET/PET Bicomponent carded IR bonded nonwoven from HDK Industries, an inner layer of NUBS breathable yet fluid impervious film from P&G, and a second outer nonwoven of 30 gsm PET/PET Bicomponent. The laminate has advantages of increased flexibility and breathability vs. glued laminates. A flexible fabric that can be custom painted/drawn/printed may be formed from a first outer nonwoven such as 30 gsm PET/PET Bicomponent carded IR bonded nonwoven from HDK Industries, an inner layer comprising a 42 gsm Bounty™ paper towel, and a second outer nonwoven of 30 gsm PET/PET Bicomponent. The inner layer of Bounty™ may be pre-printed with any conceivable text, design or logo prior to lamination that will show through the outer nonwovens. Alternately, the inner paper layer may be non-printed, and the composite may be painted or drawn upon after lamination (i.e., for children's art/play activities). The laminate may be non-apertured or apertured. The outer nonwoven layers provide a soft feel, the inner paper layer retains the color (paint, ink, etc.) and the combined laminate has the flexibility and strength of traditional knitted/woven fabrics.

Alternative uses of the laminates of the present invention include providing an inexpensive source of cooling in locations where traditional air conditioners are not available or practical. The laminate may be formed from a first outer layer of nonwoven material such as 30 gsm LDPE SB nonwoven from Corovin/BBA, an inner layer comprising a 42 gsm Bounty™ paper towel and a second outer nonwoven of 30 gsm LDPE SB. The laminate may be non-apertured or apertured, although an apertured version of the laminate is preferable in order to maximize surface area. The cooling system works by dipping one end of the laminate into a trough of water and hanging the opposite end of the laminate over an air flow exposed area, such as an open window. Alternately, the source of air flow may be artificial, such as a fan. The water from the trough wicks within the laminate via the inner paper layer, and the cooling effect comes from the evaporation of the water from the laminate into the surrounding air.

Other applications of the present invention include the use of conductive and sensorized laminates used as floor coverings. Future offices and homes are envisioned to have "smart" capabilities, able to sense the number and location of occupants. These conductive, textile-like laminates of the present invention can be used under existing carpets or incorporated into area rugs to be used as part of an integrated sensor system. Several position detector techniques could be used along with laminates of the present invention, for example, creating an X-Y array of the materials so that intersection points are formed. Upon application of foot pressure, the change in capacitance at the intersection points can be detected with the appropriate sensor technology. It is believed that use of such laminates of the present invention permit larger widths of materials to be produced, consistent with floor covering dimensions, and at much lower cost than currently available materials.

The combination of breathability and conductivity of the laminates of the present invention is well suited for incorporation into clothing. One skilled in the art can imagine a variety of electronic possibilities which can be enabled via the incorporation of such low cost, cloth-like conductive materials. Conductive laminates of the present invention can be incorporated into clothing to provide interactive capabilities. For example, when such laminates are sewn into children's clothes along with the appropriate capacitively coupled audio circuitry, touching the clothing with various pressures and locations can produce varying audio tones for amusement.

Laminates of the present invention can find use as a convenient way of forming dough or other edible materials. The laminate may be formed from a first outer layer of nonwoven material such as 30 gsm LDPE SB nonwoven from Corovin/BBA, an inner layer of dough and a second outer nonwoven of 27 gsm high elongation carded PP nonwoven from BBA. The outer nonwovens are purposefully chosen to have different chemical compositions that, with the regulation of calendaring heat and pressure, as well as inner dough layer thickness, will result in a weak bond between the outer nonwovens. The laminate may be non-apertured or apertured, although an apertured version of the laminate is preferable to give the dough a decorative shape. Ease of handling is a major benefit of the laminated dough, both in processing (cutting, packaging, etc.) and for consumers. Once the consumer removes the laminated dough from the package, the outer nonwovens can easily be removed, exposing the pre-formed dough. Alternately, the outer nonwovens can be starch bonded edible webs that can be used in this process to help form the inner dough layer, but which do not have to be removed by the consumer prior to cooking and/or consumption.

Another use for the laminates of the present invention is for use as an absorbent food pad. This thin absorbent pad is commonly placed below the food article to absorb any standing fluids in a packaged food product. Perishable food, particularly meats and poultry, are often sold with an absorbent pad placed between the perishable food and a tray. The absorbent pad will absorb any standing fluids, such as blood or other fluids which may escape from the packaged food. The laminate web used to make the absorbent food pad could be of any of the laminates described. Particularly useful are laminate webs having a highly absorbent central layer, such as single or multiple layers of Bounty Paper towels or air laid fiber core containing super absorbent fibers or super absorbent particles. The outer layers may be any suitable film or nonwoven which allows the fluid to be absorbed by the central layer. The outer layer may or may not be apertured.

Laminates of the present invention could also be used to make clean room wipes. A highly absorbent layer is used as the center layer and the outer layers are comprised of fluid control layers that would allow liquid passage into the absorbent center layer without releasing lint. This product would be desired over other products in which the absorbent material, commonly comprised of short fibers (cellulose), leaves behind particles or lint after cleaning. In the laminate of the present invention, the absorbent material is encapsulated by the outer layers thereby reducing the amount of lint left behind and controlling the fluid flow properties. Suitable outer layer materials include Tredegar 100 mesh LLDPE film, Tredegar CPM, Donalow Phillic SB PE, and other similar materials. The absorbent center layer may be Bounty™ paper towel or other absorbent material. The laminate may be non-apertured or apertured.

Tack cloths are another suitable use for laminates of the present invention. Tack cloths are used primarily to pick up small particles through mechanical entanglement or surface attraction (electrostatic or adhesive). Outer layer materials which high surface areas are desired. An apertured outer layer or apertured laminate is preferred as the apertures may form small pockets or void spaces which entrap particles. Materials with the correct electrostatic nature are preferred.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent food pad comprising a laminate web comprising:
    a) a first web;
    b) a second web joined to said first web in a face-to-face relationship at a plurality of discrete bond sites, the first and second webs forming an interior region therebetween;
    c) said bond site defining an elongated melt weakened region having an aspect ratio of at least about 3; and
    d) a third material involved in said discrete bond sites and substantially filling said interior region, wherein said third material is selected from the group consisting of paper, tissue paper, closed or oven cell foam, air laid fiber core, super absorbent particles, and combinations thereof.

2. A clean room wipe comprising a laminate web comprising:
    a) a first web;
    b) a second web joined to said first web in a face-to-face relationship at a plurality of discrete bond sites, the first and second webs forming an interior region therebetween;
    c) said bond site defining an elongated melt weakened region having an aspect ratio of at least about 3; and
    d) a third material involved in said discrete bond sites and substantially filling said interior region, wherein said third material is selected from the group consisting of paper, tissue paper, closed or open cell foam, air laid fiber core, super absorbent particles, and combinations thereof.

3. A tack cloth comprising a laminate web comprising:
    a) a first web;
    b) a second web joined to said first web in a face-to-face relationship at a plurality of discrete bond sites, the first and second webs forming an interior region therebetween;
    c) said bond site defining an elongated melt weakened region having an aspect ratio of at least about 3; and
    d) a third material involved in said discrete bond sites and substantially filling said interior region, wherein said third material is selected from the group consisting of paper, tissue paper, closed or open cell foam, air laid fiber core, super absorbent particles, and combinations thereof.

4. The absorbent food pad of claim 1 wherein the first or second web comprises a film.

5. The absorbent food pad of claim 1 wherein the first and second webs are identical.

6. An absorbent food pad comprising a laminate web comprising:
    a) a first web comprised of a film;
    b) a second web comprised of a film joined to said first web in a face-to-face relationship at a plurality of discrete bond sites, the first and second webs forming an interior region the between;
    c) said bond site defining an elongated melt weakened region having an aspect ratio of at least about 3; and
    d) a third material comprising an air laid fiber core containing super absorbent fibers involved in said discrete bond sites and substantially filling said interior region.

7. An absorbent food pad comprising a laminate web comprising:
    e) a first web;
    t) a second web joined to said first web in a face-to-face relationship at a plurality of discrete bond sites, the first and second webs forming an interior region therebetween;
    g) said bond site defining an elongated melt weakened region having an aspect ratio of at least about 3; and
    a third material involved in said discrete bond sites and substantially filling said interior region, wherein said third material is a non-thermoplastic material.

* * * * *

UNITED STATES PATENT AND TRADEMARK OFFICE
CERTIFICATE OF CORRECTION

PATENT NO. : 6,808,791 B2
DATED : October 26, 2004
INVENTOR(S) : Curro et al.

It is certified that error appears in the above-identified patent and that said Letters Patent is hereby corrected as shown below:

<u>Title page,</u>
Item [75], Inventors, "Alfred Franc Baldwin, Jr." should be -- Alfred Frank Baldwin, Jr. --.

Signed and Sealed this

Twenty-fifth Day of April, 2006

JON W. DUDAS
*Director of the United States Patent and Trademark Office*